United States Patent
Sughrue et al.

(10) Patent No.: US 11,354,803 B1
(45) Date of Patent: Jun. 7, 2022

(54) IDENTIFYING SPURIOUS TRACTS IN NEURO-NETWORKS

(71) Applicant: Omniscient Neurotechnology Pty Limited, Sydney (AU)

(72) Inventors: Michael Edward Sughrue, Brighton le Sands (AU); Stephane Philippe Doyen, Mount Kuring Gai (AU); Kieran Mann, San Diego, CA (US)

(73) Assignee: Omniscient Neurotechnology Pty Limited, Sydney (AU)

( * ) Notice: Subject to any disclaimer, the term of this patent is extended or adjusted under 35 U.S.C. 154(b) by 0 days.

(21) Appl. No.: 17/542,261

(22) Filed: Dec. 3, 2021

(51) Int. Cl.
  *G06T 7/00* (2017.01)
  *G16H 30/20* (2018.01)
  *G16H 30/40* (2018.01)

(52) U.S. Cl.
  CPC .......... *G06T 7/0012* (2013.01); *G16H 30/20* (2018.01); *G16H 30/40* (2018.01); *G06T 2207/10092* (2013.01); *G06T 2207/20024* (2013.01); *G06T 2207/20081* (2013.01); *G06T 2207/20084* (2013.01); *G06T 2207/30016* (2013.01)

(58) Field of Classification Search
  None
  See application file for complete search history.

(56) References Cited

U.S. PATENT DOCUMENTS

| | | | | |
|---|---|---|---|---|
| 2006/0281987 A1* | 12/2006 | Bartesaghi | ................ | G06T 7/11 600/410 |
| 2016/0070436 A1* | 3/2016 | Thomas | ................ | A61B 6/037 715/771 |
| 2016/0110911 A1* | 4/2016 | Frank | ..................... | A61B 5/055 382/131 |
| 2016/0155232 A1* | 6/2016 | Sela | ....................... | G06T 19/003 382/103 |
| 2017/0221208 A1* | 8/2017 | Dyer | .................. | G01R 33/5608 |
| 2017/0285124 A1* | 10/2017 | Verma | ................ | G01R 33/5608 |

(Continued)

OTHER PUBLICATIONS

Mori, S., & Van Zijl, P. C. (2002). Fiber tracking: principles and strategies—a technical review. NMR in Biomedicine: An International Journal Devoted to the Development and Application of Magnetic Resonance In Vivo, 15(7-8), 468-480. (Year: 2002).*

(Continued)

*Primary Examiner* — Samah A Beg
(74) *Attorney, Agent, or Firm* — Fish & Richardson P.C.

(57) ABSTRACT

Methods, systems, and apparatus, including computer programs encoded on a computer storage medium, for filtering a set of tracts that are predicted to be included in a selected neuro-network. In one aspect, a method comprises: receiving selection data selecting a network of a brain, processing magnetic resonance image data of the brain to identify a set of tracts that are predicted to be included in the selected network, determining a blocking surface for the selected network, comprising: obtaining a set of parcellations for the selected network and determining, based on a respective position in the brain of each parcellation in the set of parcellations, a set of parameters defining the blocking surface, and generating filtered tract data by filtering the set of tracts that are predicted to be included in the selected network to remove tracts that intersect the blocking surface.

20 Claims, 15 Drawing Sheets

NETWORK VISUALIZATION – MODIFYING
THE BLOCKING SURFACE

(56) References Cited

U.S. PATENT DOCUMENTS

2018/0098700 A1* 4/2018 Prchkovska .......... G06T 7/0012

OTHER PUBLICATIONS

Schilling, K. G. et al. (2020). Brain connections derived from diffusion MRI tractography can be highly anatomically accurate—if we know where white matter pathways start, where they end, and where they do not go. Brain Structure and Function, 225(8), 2387-2402. (Year: 2020).*

Wassermann, D., Makris, N., Rathi, Y., Shenton, M., Kikinis, R., Kubicki, M., & Westin, C. F. (2016). The white matter query language: a novel approach for describing human white matter anatomy. Brain Structure and Function, 221(9), 4705-4721. (Year: 2016).*

* cited by examiner

BLOCKING SURFACE FILTERING CRITERION

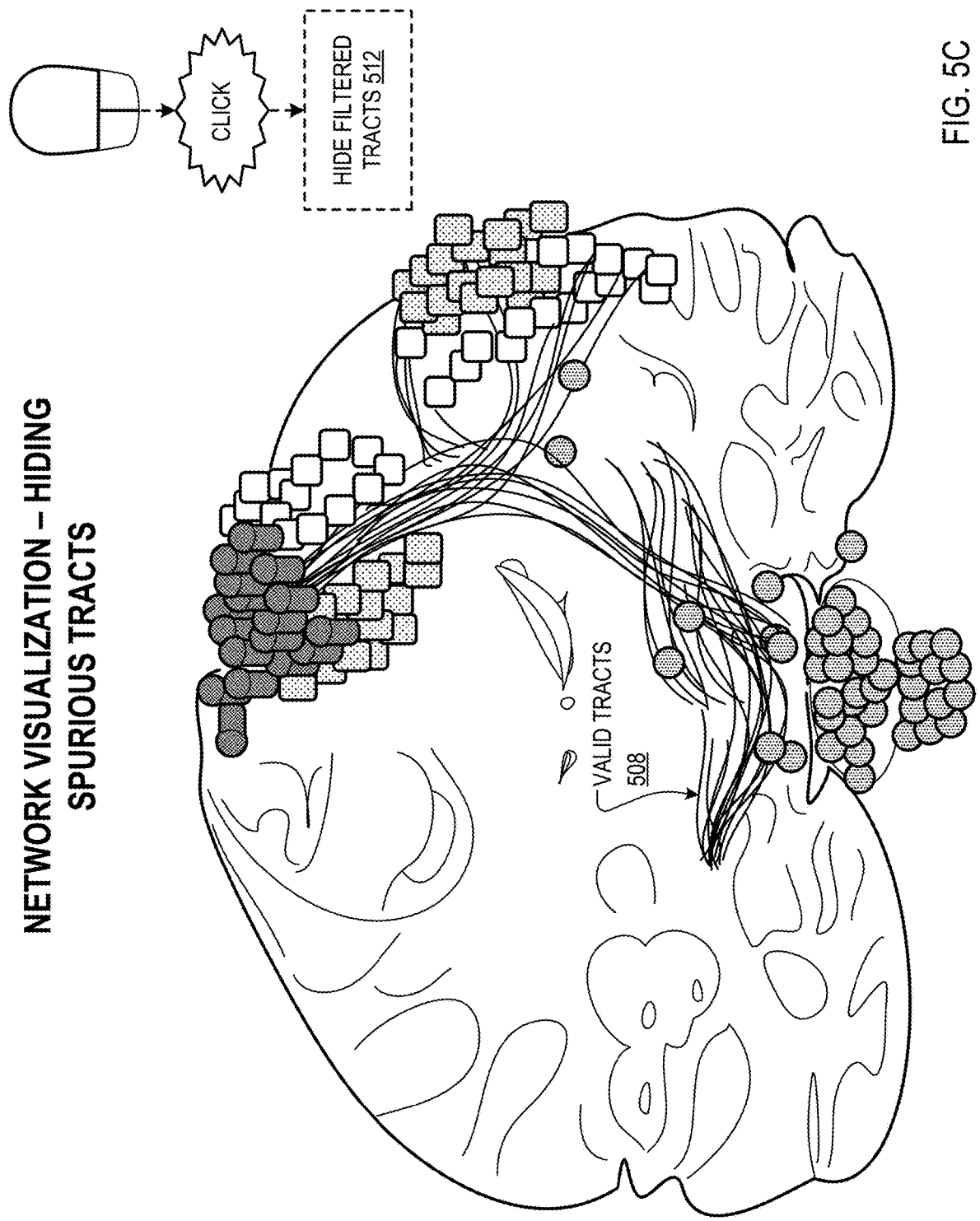

IDENTIFYING SPURIOUS TRACTS IN NEURO-NETWORKS

TECHNICAL FIELD

This specification relates to processing medical images.

BACKGROUND

Medical imaging includes techniques and processes for creating visual representations of an interior of a body for clinical analysis and medical intervention, as well as visual representation of physiology of some organs or tissues. Medical imaging can reveal internal structures hidden by skin and bones, and can be used to diagnose and treat various diseases. Medical imaging also can establish a database of normal anatomy and physiology to make it possible to identify abnormalities amongst cohorts. Some medical imaging can also provide insights into functional activity and structural connections of a brain.

SUMMARY

This specification generally describes technologies for processing medical images of brains and/or displaying the processed images in a user-interactive brain navigation system (e.g., interface). The disclosed technology can be used by clinicians and other medical professionals to glean insight about structures and connections in the brain of a subject. Based on such insights, the clinicians and other medical professionals can perform improved and more informed diagnoses, treatments, operations, and/or research than with existing systems.

Throughout this specification, a "subject" can refer to, e.g., a patient, human, animal, or other specimen.

A "parcellation" in a brain refers to a region, e.g., a three-dimensional (3D) volumetric region, of the brain. Typically, a parcellation refers to a region that has a specified function, structural connectivity, or cellular composition.

A collection of parcellations that collectively define a partition of the brain may be referred to as a "parcellation atlas." A parcellation atlas can include any appropriate number of parcellations, e.g., 50 parcellations, 100 parcellations, 500 parcellations, or 1000 parcellations. In one embodiment, a parcellation atlas can include 379 parcellations. A partition of a brain into a set of parcellations from a parcellation atlas can be represented, e.g., by associating each voxel in an image of the brain with an index of a respective parcellation that includes the voxel. Voxels in an image of a brain can be assigned to parcellations using systems and methods described in U.S. Pat. Nos. 11,055,849 and 11,145,119 which are incorporated by reference herein in their entirety.

Generally, a parcellation atlas can be chosen such that each parcellation in the parcellation atlas is expected to have broadly similar properties (e.g., functional activity, structural connectivity, or cellular composition) between subjects, even if the boundaries of the parcellation differ between subjects. The boundaries of parcellations may differ between subjects because of structural differences between the brains of subjects. In particular, the boundaries of parcellations in the brain of a subject can depend on the size of the brain, the shape of the brain, the presence of abnormalities (e.g., tumors) in the brain (e.g., that have the effect of distorting and displacing the remaining normal brain tissue), and on whether portions of the brain have been resected (e.g., surgically removed).

A "tract" or "nerve tract" in a brain can refer to one or more axons (nerve fibers) in the brain, e.g., in the white matter of the brain. A tract in a brain can be visually represented, e.g., as a line or tube that traces a path through a 3D model representing the brain. A tract can be represented in numerical format, e.g., by a collection of 3D numerical coordinates (e.g., x-y-z Cartesian coordinates expressed in a frame of reference of the brain) that are each positioned at a respective location on the tract.

A "network" in a brain can refer to a bundle (group) of multiple tracts that collectively form a structure and/or a functional network in the brain. For example, a network can include a bundle of tracts that link a set of regions in the brain, e.g., regions associated with respective functions, e.g., perceptual functions and memory functions. Examples of possible networks include a corticospinal network, a superior longitudinal fasciculus network, a cingulum network, an inferior fronto-occipital fascicle network, a frontal aslant tract network, a uncinated fasciculus network, an inferior longitudinal fasciculus network, a middle longitudinal fascicle network, a vertical occipital fasciculus network, and an optic radiations network.

According to one aspect, there is provided a method comprising: receiving selection data selecting a network of a brain; processing magnetic resonance image data of the brain to identify a set of tracts that are predicted to be included in the selected network; determining a blocking surface for the selected network, comprising: obtaining a set of parcellations for the selected network; and determining, based on a respective position in the brain of each parcellation in the set of parcellations, a set of parameters defining the blocking surface; generating filtered tract data by filtering the set of tracts that are predicted to be included in the selected network to remove tracts that intersect the blocking surface; and taking an action based at least in part on the filtered tract data.

In some implementations, determining the set of parcellations defining the blocking surface comprises: determining a respective central position, in the brain, of each parcellation in the set of parcellations corresponding to the selected network; and determining the set of parameters defining the blocking surface based on the respective central position, in the brain, of each parcellation in the set of parcellations corresponding to the selected network.

In some implementations, determining the set of parcellations defining the blocking surface based on the respective central position, in the brain, of each parcellation in the set of parcellations corresponding to the selected network comprises: estimating a convex hull of the central positions of the parcellations in the set of parcellations corresponding to the selected network; and determining the set of parameters defining the blocking surface based on the convex hull of the central positions of the parcellations in the set of parcellations corresponding to the selected network.

In some implementations, the blocking surface comprises a surface of the convex hull of the central positions of the parcellations in the set of parcellations corresponding to the selected network.

In some implementations, determining the set of parameters defining the blocking surface based on the respective central position, in the brain, of each parcellation in the set of parcellations corresponding to the selected network comprises: performing an optimization to determine a set of parameters defining a planar surface that minimizes an error between: (i) the planar surface, and (ii) the respective central position of each parcellation in the set of parcellations corresponding to the selected network.

In some implementations, the optimization comprises a least-squares optimization.

In some implementations, for each parcellation in the set of parcellations corresponding to the selected network, the central position of the parcellation is a centroid of the parcellation.

In some implementations, the blocking surface is a two-dimensional surface.

In some implementations, the blocking surface is a planar surface.

In some implementations, the blocking surface is a surface of a convex polytope.

In some implementations, the set of parcellations corresponding to the selected network comprises at least three parcellations.

In some implementations, the magnetic resonance image data of the brain comprises diffusion-weighted magnetic resonance image data.

In some implementations, the selected network of the brain is selected from a group comprising one or more of: a corticospinal network, a superior longitudinal fasciculus network, a cingulum network, a frontal aslant tract network, a uncinated fasciculus network, an inferior longitudinal fasciculus network, a middle longitudinal fascicle network, a vertical occipital fasciculus network, or an optic radiations network.

In some implementations, generating filtered tract data by filtering the set of tracts that are predicted to be included in the selected network to remove tracts that intersect the blocking surface comprises: identifying tracts that intersect the blocking surface as being spurious tracts.

In some implementations, taking an action based at least in part on the filtered tract data comprises: providing a visualization of the filtered tract data for display on a user computing device.

In some implementations, taking an action based at least in part on the filtered tract data comprises: using the filtered tract data to guide a surgical procedure.

In some implementations, taking an action based at least in part on the filtered tract data comprises: using the filtered tract data to select a drug to be administered to a subject.

In some implementations, taking an action based at least in part on the filtered tract data comprises: using the filtered tract data to plan a transcranial magnetic stimulation procedure.

According to another aspect there is provided a system comprising: one or more computers; and one or more storage devices communicatively coupled to the one or more computers, wherein the one or more storage devices store instructions that, when executed by the one or more computers, cause the one or more computers to perform operations of the methods described herein.

One or more non-transitory computer storage media storing instructions that when executed by one or more computers cause the one or more computers to perform operations of the methods described herein.

Particular embodiments of the subject matter described in this specification can be implemented so as to realize one or more of the following advantages.

This specification describes a tract processing system that can process a magnetic resonance image (MRI) of a brain of a subject to identify one or more networks in the brain of the subject. In particular, the tract processing system can determine, for each network, a respective set of tracts in the brain of the subject that are predicted to be included in the network. In some cases, a set of tracts that are predicted to be part of a network can include one or more "spurious" tracts, i.e., that are incorrectly designated as being part of the network. The tract processing system can increase the accuracy and validity of a set of tracts that are predicted to be part of a network by "filtering" the set of tracts to identify and remove spurious tracts, thus producing a set of "filtered" or "valid" tracts.

To filter spurious tracts from a set of tracts that are predicted to be included in a network, the tract processing system can determine a "blocking surface," i.e., a two-dimensional (2D) surface (manifold) defined in the frame of reference of the brain of the subject. The blocking surface defines a criterion for identifying spurious tracts, e.g., tracts that intersect the blocking surface may be designated as being spurious tracts. The tract processing system can determine the blocking surface for a network using a set, e.g., a predefined set, of parcellations for, e.g., assigned to, the network, which are referred to for convenience as "blocking" parcellations. For example, the tract processing system can perform a numerical optimization to fit the blocking surface to the respective centroid of each blocking parcellation in the brain of the subject, as will be described in more detail below.

The positions of the blocking parcellations for a network will generally differ between subjects as a result of structural differences between the brains of subjects, as described above. As a result, the position, the orientation (and/or possibly, the shape) of the blocking surface for the network, which is fitted to the blocking parcellations for the network, can also differ between subjects. Thus the blocking surface defines a subject-specific tract filtering criterion that automatically identifies and filters spurious tracts in a manner that is adapted for the networks of each subject and can therefore achieve a high level of accuracy (i.e., in identifying spurious tracts). In contrast, using a predefined blocking surface that is not adapted to each subject may yield significantly worse (e.g., less accurate) results in filtering spurious tracts, e.g., by missing spurious tracts, by improperly identifying valid tracts as being spurious, or both.

This specification further describes an interface system that, in response to receiving a request to display a visualization of a network, can render a three-dimensional (3D) spatial visualization of the network that shows both: (i) valid (i.e., filtered) tract data, and (ii) spurious tract data, for the network. The interface system can visually distinguish the spurious tracts from the valid tracts, e.g., by displaying the spurious tracts in a different color than the valid tracts, or with a different transparency than the valid tracts, or both. The interface system can enable the user to interact with the network visualization, e.g., by partially or completely reversing the spurious tract filtering (e.g., such that some or all of the spurious tracts are re-designated as valid tracts), by hiding the spurious tracts, or by modifying the blocking surface used to identify the spurious tracts.

Filtering spurious tracts from a network, e.g., using a blocking surface, provides an efficient and automated way to improve the accuracy and interpretive value of a network visualization. However, an incorrect filtering criterion could, in some cases, incorrectly identify certain valid tracts as being spurious tracts. By including the spurious tracts in the network visualization, but visually distinguishing them from the valid tracts, the interface system can enable a user to detect and correct possible errors in the tract filtering or double check/validate a correct tract filtering.

Generating a network visualization that entirely excludes tracts identified as being spurious tracts would result in spurious tracts being identified and filtered without user supervision, and in particular, a user could not detect when valid tracts have been improperly filtered. However, refraining from identifying and filtering spurious tracts may diminish the accuracy and interpretive value of the network visualization. By including spurious tracts in the network visualization, but visually distinguishing them from valid tracts, the interface system can achieve the benefits of automated tract filtering (e.g., increased accuracy and interpretive value) while reducing any associated risks (e.g., valid tracts being improperly filtered). Thus the interface system provides an improvement in the field of user interface technology.

Deploying automated medical image processing technology in clinical workflows involving the treatment of subjects requires a high level of confidence, by users, that the automated techniques rarely (if ever) yield inaccurate results. By including spurious tracts in the network visualization, but visually distinguishing them from valid tracts, the interface system can enable users to detect and correct possible errors in tract filtering, and therefore enable automated tract filtering techniques to be incorporated in clinical workflows. Thus the interface system provides an improvement in the field of automated image processing technology.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIG. 5A-D illustrates example of network visualizations.

Like reference numbers and designations in the various drawings indicate like elements.

DETAILED DESCRIPTION

This specification describes a tract processing system and an interface system. An example of a tract processing system will be described in more detail below with reference to FIG. 1. An example of an interface system will be described in more detail below with reference to FIG. 4.

The tract processing system and the interface system can be implemented as part of a broader computer system that can optionally provide additional functionality and perform additional operations, e.g., involving processing medical images of brains and/or displaying the processed images. An example computer system that can implement the tract processing system and the interface system will be described in more detail below with reference to FIG. 9.

Figure 1:
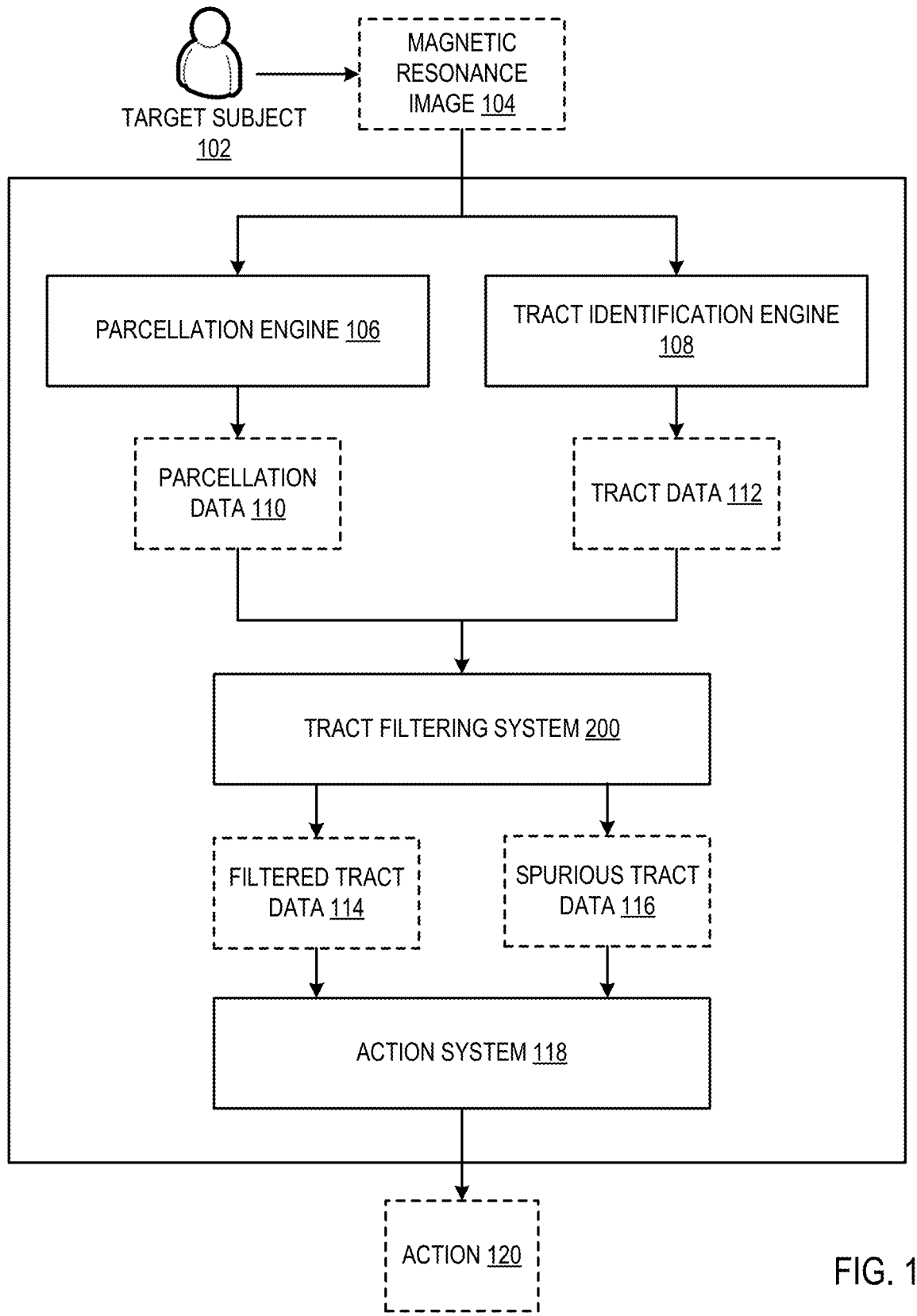
FIG. 1 shows an example tract processing system.

FIG. 1 shows an example tract processing system 100. The tract processing system 100 is an example of a system implemented as computer programs on one or more computers in one or more locations in which the systems, components, and techniques described below are implemented.

The tract processing system 100 is configured to receive MRI image data 104 (also referred to simply as an Mill image) showing the brain data of a target subject 102. The tract processing system 100 can receive the MM image 104 for the target subject 102, e.g., directly from a medical imaging device (e.g., an MM imaging device) that generated the MRI image 104, or by retrieving the MRI image 104 from a data store.

The Mill image 104 can be any appropriate image, acquired by magnetic resonance imaging techniques, that enables identification and localization of tracts in the brain of the target subject 102. For example, the MRI image 104 can be a diffusion-weighted MRI image, e.g., a diffusion tensor image, that characterizes strength and directionality of water diffusion at each voxel in a 3D grid of voxels that covers the brain of target subject 102. The MM image 104 can be represented in any appropriate numerical format, e.g., as an ordered collection of numerical values, e.g., as a matrix or tensor of numerical values.

The tract processing system 100 includes a parcellation engine 106, a tract identification engine 108, a tract filtering system 200, and an action system 118, which are each described in more detail next.

The parcellation engine 106 is configured to process the MRI image 104 to generate parcellation data 110 that defines a partition of the brain of the target subject into a set of parcellations from a parcellation atlas. The parcellation engine 106 can generate the parcellation data 110 for the brain of the target subject 102 using any appropriate parcellation technique.

For example, the parcellation engine 106 can generate the parcellation data 110 for the brain of the target subject using "reference" parcellation data for the brain of a "reference" subject. The reference parcellation data for the brain of the reference subject defines a partition of an MRI image of the brain of the reference subject into the set of parcellations from the parcellation atlas.

The parcellation engine 106 can register an atlas to the MRI image of the brain of the target subject 102. That is, the parcellation engine 106 can determine the parameters of a "warping" transformation (e.g., an affine or elastic transformation) that aligns an atlas to the MRI image of the brain of the target subject 102. The parcellation engine 106 can assign voxels to parcellations from the atlas to map each parcellation onto a corresponding region of the brain of the target subject 102, thus generating the parcellation data 110 for the brain of the target subject 102.

The tract identification engine 108 is configured to process the MM image 104 of the brain of the target subject 102 to generate respective tract data 112 for each network in a predefined set of networks. The tract data 112 for a network identifies a set of tracts in the brain of the target subject 102 that are predicted to be included in the network. The predefined set of networks can include any appropriate number of networks, e.g., 1, 10, or 50 networks. Examples of possible networks are described above.

To generate the tract data 112, the tract identification engine 108 applies a tractography algorithm to the MRI image 104 of the brain of the target subject 102 to identify a set, e.g., a full set, of tracts that are included in the brain of the target subject 102. The tract identification engine 108 can use any appropriate tractography algorithm to identify the tracts in the brain of the target subject 102. Generally, a tractography algorithm can identify tracts in the brain of a subject based on patterns of water diffusion represented by an MM image of the brain, e.g., by mapping paths through the brain along which water preferentially diffuses. An example of a tractography algorithm is described with reference to, e.g.: Peter J. Basser et al., "In vivo fiber tractography using DT-MM data," *Magnetic Resonance in Medicine*, Volume 44, Issue 4, p. 625-632 (2000).

After performing tractography to identify the tracts in the brain of the target subject 102, the tract identification engine 108 identifies, for each network, a respective set of tracts that are predicted to be included in the network. The tract identification engine 108 can identify the set of tracts that are predicted to be included in a given network in any appropriate manner, e.g., 1) in accordance with a set of predefined rules or criteria, 2) based on location of the tract in question and/or brain regions the tract in question connects, or 3) a combination of (1) and (2). In one example, a network may be associated with a particular parcellation, and the tract identification engine 108 may identify any tract that passes through the particular parcellation as being included in the network. In another example, a network may be associated with a set of two or more parcellations, and the tract identification engine 108 may identify any tract that passes through all the parcellations in set of parcellations associated with the network as being included in the network. In yet another example, if a given tract starts in one parcellation and ends in the same or another parcellation belonging to a given network, the system associates the tract with that network. Additional example techniques for identifying a set of tracts that are predicted to be included in a given network are described with reference to U.S. Pat. No. 11,145,119 which is incorporated by reference herein.

Generally, the brain can include a large number of tracts, and these tracts can exhibit complex and unpredictable behavior. As a result of this complexity, the rules or criteria used by the tract identification engine 108 to classify tracts as being included in corresponding networks may be inadequate to achieve perfect tract classification. In particular, the tract data 112 for a network can, in some cases, include one or more spurious tracts, i.e., tracts that the tract identification engine 108 has incorrectly identified as being included in the network.

The tract filtering system 200 is configured to process the parcellation data 110 and the tract data 112 to determine, for each network, a partition of tract data 112 for the network into: (i) filtered (or "valid") tract data 112, and (ii) spurious tract data 116. The spurious tract data 116 for a network identifies spurious tracts from the tract data 112 for the network, and the filtered tract data 114 includes the remaining tract data 112 for the network. That is, the filtered tract data 114 for a network is a subset of the tract data 112 for the network from which the spurious tracts have been removed, or "filtered."

In some cases, the tract filtering system 200 may identify all the tracts in the tract data 112 for a network as being valid, i.e., such that the spurious tract data 116 for the network is a null set. In these cases, the filtered tract data 114 for the network may be equal to the original tract data 112 for the network.

An example of a tract filtering system 200 is described in more detail below with reference to FIG. 2.

The action system 118 is configured to perform one or more actions 120 using the filtered tract data 114 and spurious tract data 116 for the networks. A few examples of possible actions 120 that can be performed by the action system 118 are described next.

In one example, the action system 118 can make the filtered tract data 114 and the spurious tract data 116 for each network available to an interface system. The interface system can enable a user to select one or more networks, and in response to the selection, the interface system can provide visualization data for the selected networks for display on a user computing device.

In some implementations, the interface system can provide visualization data that shows, for each selected network, a respective 3D spatial representation of both: (i) the filtered tracts, and (ii) the spurious tracts, corresponding to the network, where the spurious tracts are visually distinguished from the filtered tracts. The spurious tracts can be visually distinguished from the filtered tracts, e.g., as a result of being displayed in a different color than filtered tracts, or with a different transparency than the filtered tracts, or both.

In some implementations, the interface system can provide visualization data that shows, for each selected network, a respective 3D spatial representation of only the filtered tracts corresponding to the network, i.e., such that the spurious tracts are not included in the visualization.

An example of an interface system is described in more detail below with reference to FIG. 4.

In another example, the action system 118 can store the filtered tract data 114 for each network in a data store, e.g., a logical data storage area or physical data storage device.

In another example, the action system 118 can compute one or more statistics of the filtered tract data 114 for each network, e.g., the action system 118 can compute the number of tracts included in the filtered tract data 114 for each network.

In other examples, the action system 118 can provide the filtered tract data 114 (and, optionally, the spurious tract data 116) for use guiding surgical procedures, or in determining an appropriate course of drug therapy, or in determining an appropriate course of behavioral therapy, or in planning a transcranial magnetic stimulation procedure.

Figure 2:
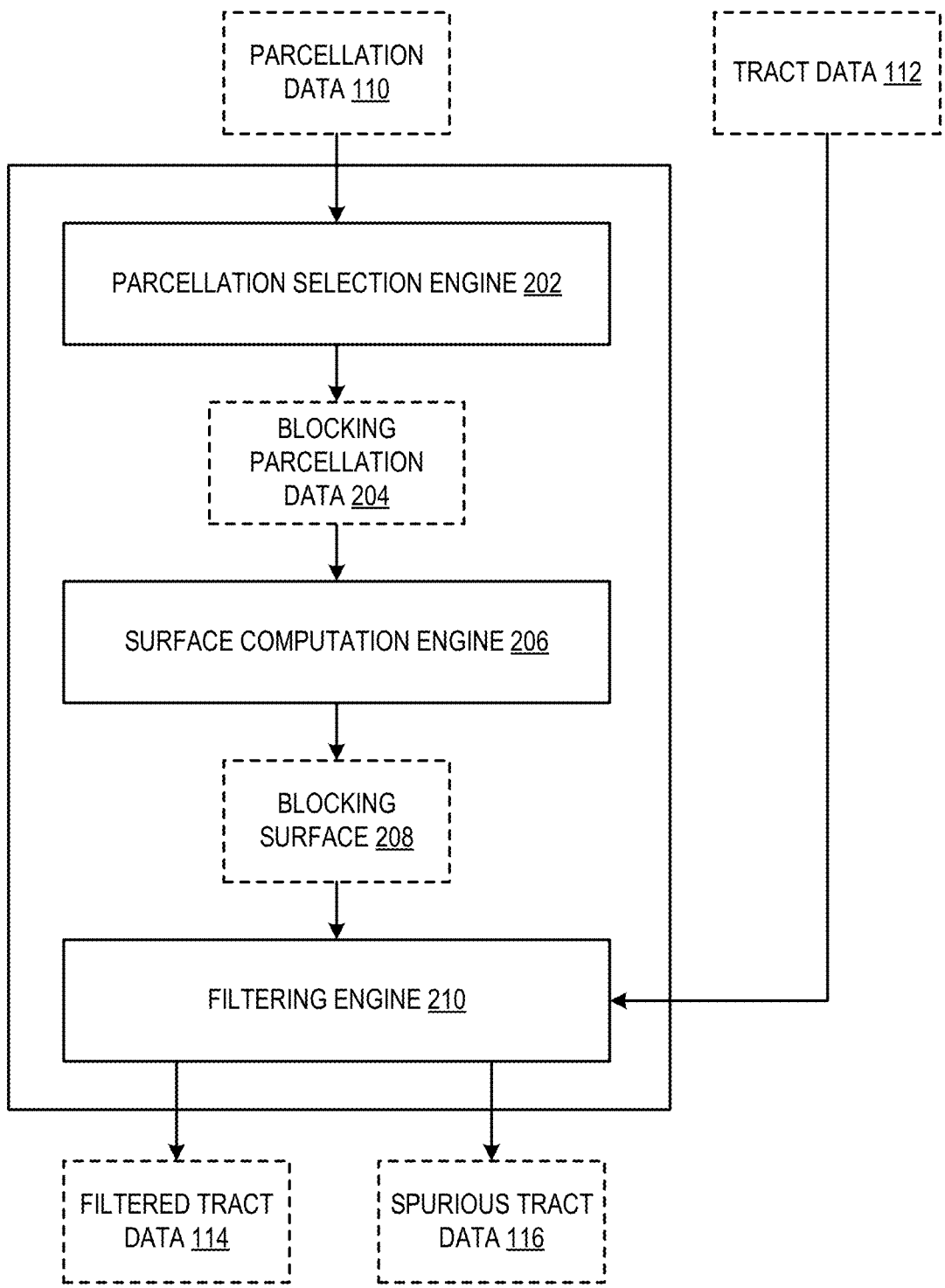
FIG. 2 shows an example tract filtering system.

FIG. 2 shows an example tract filtering system 200. The tract filtering system 200 is an example of a system implemented as computer programs on one or more computers in one or more locations in which the systems, components, and techniques described below are implemented.

The tract filtering system 200 is configured to receive: (i) parcellation data 110, and (ii) tract data 112, corresponding to each of one or more networks for a target subject. The parcellation data 110 defines a partition of the brain of the target subject into a set of parcellations from a parcellation atlas. The tract data 112 for a network identifies a set of tracts, in the brain of the target subject, that are predicted to be included in the network.

The tract filtering system 200 generates, for each network: (i) a respective set of filtered tract data 114, (ii) a respective set of spurious tract data 116. The spurious tract data 116 for a network identifies spurious tracts from the tract data 112 for the network, and the filtered tract data 114 includes the remaining tract data 112 for the network.

The tract filtering system includes a parcellation selection engine 202, a surface computation engine 206, and a filtering engine 210, which are each described in more detail next. For convenience, the following will describe operations performed by the tract filtering system 200 to generate filtered tract data 114 and spurious tract data 116 for a particular network. It can be appreciated that these operations can be performed for any appropriate number of networks (e.g., 5, 10, or 50 networks) to generate filtered tract data 114 and spurious tract data 116 for each network.

The parcellation selection engine 202 is configured to maintain data that identifies, for each network in a set of networks, a predefined set of parcellations from a parcellation atlas that are designated as being "blocking" parcellations for the network.

A set of parcellations can be designated as being blocking parcellations for a network if their respective positions within the brain of a subject can be used to construct a "blocking surface" that defines a criterion identifying spurious tracts from the tract data for the network. (Generating a blocking surface using a set of blocking parcellations, and using the blocking surface to define a criterion for identifying spurious tracts, will be described in more detail below).

The blocking parcellations for each network can be specified manually or automatically. The blocking parcellations for a network can be specified manually, e.g., by a human expert, e.g., a specialist physician, based on an analysis of the anatomy of the brain and known relationships between the routes of the networks and the spatial positions of parcellations relative to the network in question. The blocking parcellations for a network can be specified automatically, e.g., in accordance with a set of predefined or machine-learned rules. A set of blocking parcellations for a network can include any appropriate number of parcellations, and generally includes at least three parcellations. The number of blocking parcellations can vary between networks, e.g., such that certain networks can be associated with more or fewer blocking parcellations than other networks.

Generally, the set of blocking parcellations for a network is not subject-specific, i.e., the same set of parcellations are designated as being blocking parcellations irrespective of the identity of the subject. However, the spatial positions of the blocking parcellations in the brain will generally differ between subjects because of structural differences between the brains of subjects. In particular, the spatial positions of parcellations in the brain of a subject can depend on the size of the brain, the shape of the brain, the presence of abnormalities (e.g., tumors) in the brain (e.g., that have the effect of distorting and displacing the remaining normal brain tissue), and on whether portions of the brain have been resected (e.g., surgically removed).

The parcellation selection engine 202 obtains, from the parcellation data 110 for the target subject, blocking parcellation data 204 that identifies a respective spatial position in the brain of the target subject of each blocking parcellation for the network. The spatial position of a parcellation in the brain of the target subject can be represented in any appropriate way. In one example, the spatial position of a parcellation in the brain of the target subject can be represented by 3D spatial coordinates (e.g., x-y-z Cartesian coordinates) of a centroid (or other central position) of the parcellation in the brain of the target subject. In another example, the spatial position of a parcellation in the brain of the target subject can be represented by a collection of 3D spatial coordinates that each represent a respective position located inside the parcellation in the brain of the target subject.

The surface computation engine 206 is configured to process the blocking parcellation data 204 for the network to generate a set of parameters that collectively define a "blocking surface" 208 in the brain of the target subject. The blocking surface 208 is a two-dimensional (2D) surface (manifold) defined in the frame of reference of the brain of the target subject. The blocking surface 208 can be a planar surface, i.e., a "flat" surface having zero curvature at every point on the surface, or a non-planar surface, i.e., having non-zero curvature at some or all points on the surface. The blocking surface 208 defines a criterion for identifying spurious tracts from the tract data 112 for the network, as will be described in more detail below.

Generally, the blocking surface can be understood as a surface that is fitted to the positions of the blocking parcellations. The surface computation engine 206 can generate the blocking surface 208 from the blocking parcellation data 204 in any of a variety of ways. A few example techniques by which the surface computation engine 206 can generate the blocking surface 208 from the blocking parcellation data 204 are described next.

In some implementations, to generate the blocking surface 208, the surface computation engine 206 processes the blocking parcellation data 204 to determine a respective centroid (or other central point) of each blocking parcellation for the network. The surface computation engine 206 then estimates the convex hull of the centroids of the blocking parcellations for the network. The "convex hull" for a set of points (e.g., the set of centroids of the blocking parcellations) can refer to the minimal convex set that contains each point in the set of points. The convex hull for the set of centroids of the blocking parcellations may be a convex polytope, i.e., a convex region with flat sides. The surface computation engine 206 can compute the convex hull of the centroids of the blocking parcellations using any appropriate technique, e.g., using Chan's algorithm, as described with reference to: T. M. Chan, "Optimal output-sensitive convex hull algorithms in two and three dimensions," *Discrete and Computational Geometry,* 16, 361-368 (1996).

After computing the convex hull of the centroids of the blocking parcellations, the surface computation engine 206 can define the blocking surface as the surface of the convex hull. The surface computation engine 206 can numerically represent the surface of the convex hull, e.g., by a set of parameters defining the components of an m×3 matrix A and a m×1 vector b, where m is the number of faces of the convex hull, and where the surface of the convex hull is defined as the set of points $x \in \mathbb{R}^3$ satisfying:

$$A \cdot x = b \tag{1}$$

In some implementations, the surface computation engine 206 generates a planar blocking surface by performing an optimization to minimize an error between: (i) the plane, and (ii) the respective centroid of each blocking parcellation. That is, the surface computation engine 206 determines parameters $A \in \mathbb{R}$ and $b \in \mathbb{R}$ of a planar blocking surface as the result of the optimization:

$$\min_{A,b} \sum_{i=1}^{n} (A \cdot c_i - b)^2 \tag{2}$$

where i indexes the blocking parcellations, n is the number of blocking parcellations, and $c_i \in \mathbb{R}^3$ is the centroid of blocking parcellation i. The surface computation engine can perform the optimization using any appropriate optimization technique, e.g., a least-squares optimization technique.

In some implementations, the network can be associated with exactly three blocking parcellations, and the surface computation engine 206 defines the blocking surface 208 as the unique planar surface that transects the respective centroids of the three blocking parcellations.

The filtering engine 210 is configured to use the blocking surface 208 for the network to partition the tract data 112 for the network into: (i) the filtered tract data 114, and (ii) the spurious tract data 116. In particular, the filtering engine 210 uses the blocking surface 208 for the network to define a filtering criterion for identifying spurious tracts from the tract data 112 for the network. The filtering engine 210 can then identify any tract (i.e., from the tract data 112 for the network) that satisfies the filtering criterion as being a spurious tract (i.e., that should be included in the spurious tract data 116), and any tract that does not satisfy the filtering criterion as being a valid tract (i.e., that should be included in the filtered tract data 114).

Figure 3:
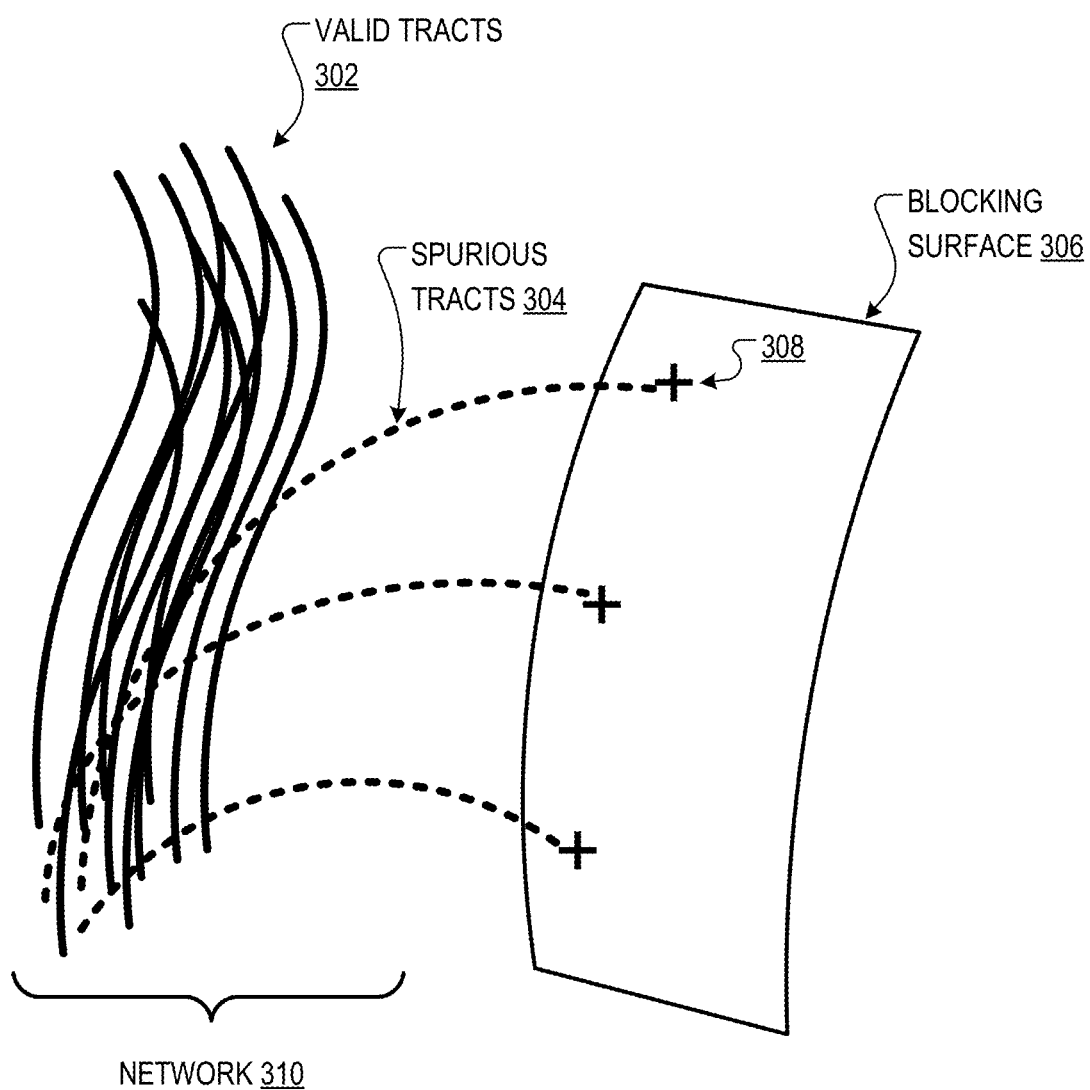
FIG. 3 illustrates an example of using a blocking surface as a filtering criterion to filter spurious tracts from a set of tracts that are predicted to be included in a network.

The filtering engine 210 can apply any appropriate filtering criterion with reference to the blocking surface 208. For example, the filtering engine 210 can identify any tract (i.e., from the tract data 112 for the network) that intersects the blocking surface 208 as satisfying the filtering criterion. As another example, the filtering engine 210 can identify any tract (i.e., from the tract data 112 for the network) that approaches within a predefined threshold distance of the blocking surface 208 as satisfying the filtering criterion. FIG. 3 illustrates an example of using a blocking surface as a filtering criterion.

In some cases, the filtering engine 210 may determine that none of the tracts for the network satisfy the filtering criterion, and thus the spurious tract data 116 may be a null set.

The positions of the blocking parcellations for a network will generally differ between subjects as a result of structural differences between the brains of subjects, as described above. As a result, the position (and possibly, the shape) of the blocking surface for the network, which is fitted to the blocking parcellations for the network, will also differ between subjects. Thus the blocking surface defines a subject-specific tract filtering criterion that automatically identifies and filters spurious tracts in a manner that is optimized for each subject. In contrast, using a predefined blocking surface that is not adapted to each patient may yield significantly worse (e.g., less accurate) results in filtering spurious tracts, e.g., by missing spurious tracts, by improperly identifying valid tracts as being spurious, or both.

The tract filtering system 200 can repeat the operations described above for each of a set of networks to generate respective filtered tract data 114 and spurious tract data 116 for each network in the set of networks. The tract filtering system 200 can provide the filtered tract data 114 and the spurious tract data 116, e.g., to the tract processing system 100 described with reference to FIG. 1, or to the interface system described with reference to FIG. 4.

FIG. 3 illustrates an example of using a blocking surface 306 as a filtering criterion to filter spurious tracts 304 from a set of tracts that are predicted to be included in a network 310. In particular, tracts that intersect the blocking surface 306 (e.g., at location 308) can be identified as spurious tracts 304, i.e., that are not included in the network 310. The remaining tracts that do not intersect the blocking surface 306 can be identified as valid tracts 302, i.e., that are included in the network 310.

Figure 4:
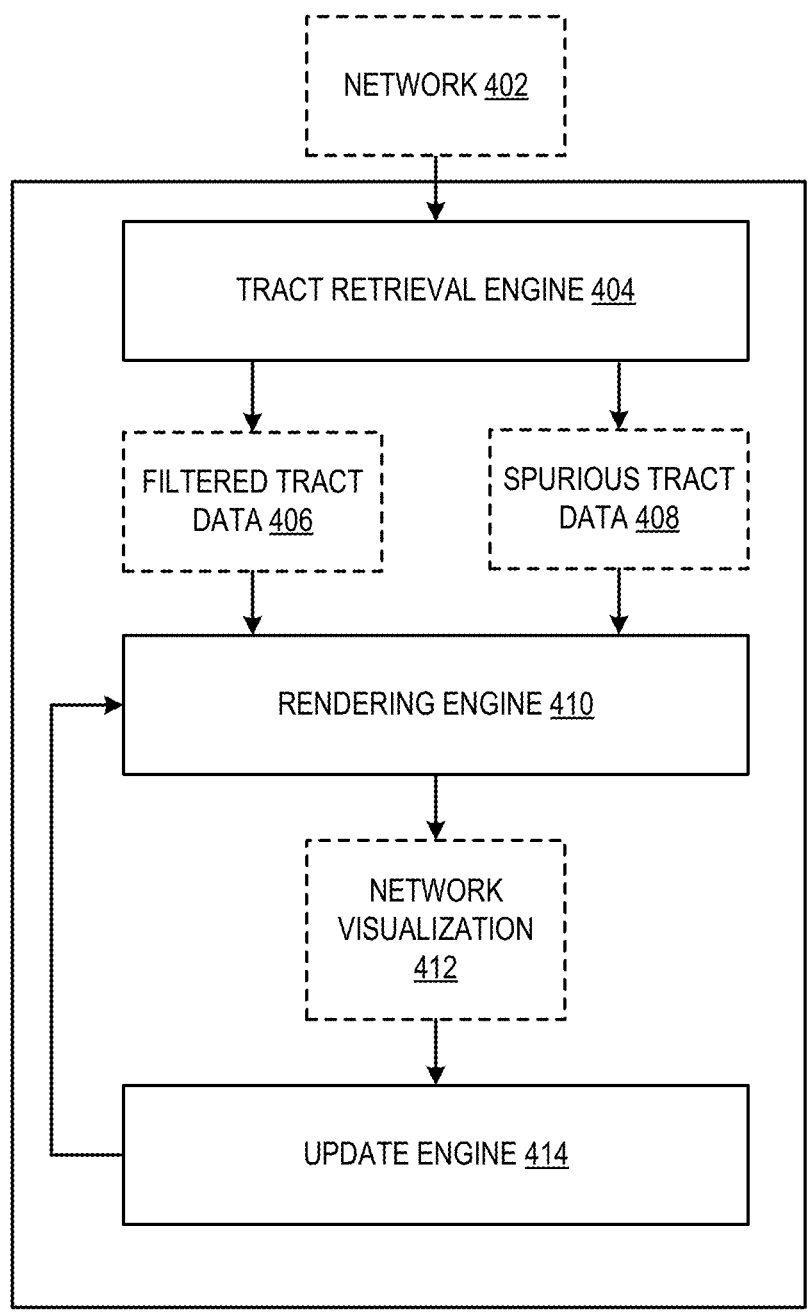
FIG. 4 shows an example interface system.

FIG. 4 shows an example interface system 400. The interface system 400 is an example of a system implemented as computer programs on one or more computers in one or more locations in which the systems, components, and techniques described below are implemented.

The interface system 400 generates visualizations of networks in the brain of a target subject using a tract retrieval engine 404, a rendering engine 410, and an update engine 414, which are each described in more detail below.

The interface system 400 is configured to make a user interface available to a user by way of a user computing device. The user interface enables the user to select a network 402, e.g., from a predefined set of networks. By selecting a network, the user makes a request to be presented with a visualization of the network.

In response to receiving the selection of the network 402 from the user, the tract retrieval engine 404 obtains: (i) filtered tract data 406, and (ii) spurious tract data 408, for the network. The filtered tract data 406 identifies tracts, in the brain of the target subject, that are predicted to be included in the network. The spurious tract data 408 identifies tracts, in the brain of the target subject, that were initially predicted to be included in the network but which were subsequently identified as being spurious tracts that are not included in the network.

The filtered tract data 406 and the spurious tract data 408 for the network 402 can be generated by a tract processing system, e.g., the tract processing system 100 described with reference to FIG. 1. The tract processing system 100 generates filtered tract data 406 for a network by filtering a set of tracts that are predicted to be included in the network using a filtering criterion based on a blocking surface, as described above. However, the interface system 400 is not limited to working in conjunction with the tract processing system 100 described with reference to FIG. 1. In particular, the interface system 400 can obtain filtered tract data 406 and spurious tract data 408 from any system that can process an MRI image of the brain of the target subject to generate filtered tract data 406 and spurious tract data 408 for the networks in the brain of the target subject.

The filtered tract data 406 and the spurious tract data 408 for the network 402 may be pre-computed, i.e., rather than being dynamically generated by a tract processing system in response to a request from the user to be presented with a visualization of the network 402. That is, the tract retrieval engine 404 may retrieve the filtered tract data 406 and the spurious tract data 408 from a data store where the filtered tract data 406 and the spurious tract data 408 was previously stored after being generated by the tract processing system.

The rendering engine 410 is configured to generate (render) a 3D spatial visualization 412 of the network 402 that includes the filtered tract data 406, and optionally, the spurious tract data 408. (The visualization 412 may include the spurious tract data 408, e.g., to enable the user to reverse the filtering of the network, as will be described in more detail below).

The visualization 412 can display the tracts associated with the network 402 (i.e., the filtered tracts 406, and optionally, the spurious tracts 408) as part of a 3D model of the brain of the target subject. Each individual tract can be displayed, e.g., as a line or tube that traces a corresponding path through the 3D model of the brain of the target subject. The 3D model of the brain of the target subject can optionally represent other features of the brain of the target subject in addition to the network 402, e.g., the positions of specified parcellations, or the positions of abnormalities in the brain, e.g., the sites of tumors.

If the visualization 412 includes the spurious tract data 408, then the visualization 412 can visually distinguish the spurious tract data 408 from the filtered tract data 406, e.g., to enable the user to easily distinguish between the filtered tract data 406 and the spurious tract data 408. The visualization 412 can visually distinguish between the filtered tract data 406 and the spurious tract data 408 in any of a variety of possible ways. For example, the visualization 412 can display the filtered tracts 406 as having a different color than the spurious tracts 408, e.g., the filtered tracts 406 can be displayed with a green color while the spurious tracts 408 can be displayed with a red color. As another example, the visualization can display the filtered tracts 406 with a different transparency than the spurious tracts 408, e.g., the filtered tracts 406 can be displayed as being opaque while the spurious tracts 408 can be displayed as being at least partially transparent. As another example, the visualization 412 can display the filtered tracts 406 as having both a different color and a different transparency than the spurious tracts 408.

The interface system 400 can provide the visualization 412 of the network 402 for display on the user computing device, e.g., on a screen of the user computing device. The user can reference the visualization 412 of the network 402, e.g., as part of diagnosing a medical condition in the target subject, or as part of providing a treatment or therapy to the target subject. For example, the user can reference the visualization 412 to assist in planning a surgical procedure, e.g., to plan the surgical procedure in a manner that reduces the likelihood of significant damage to the network. As another example, the user can reference the visualization 412 to assist in planning a transcranial magnetic stimulation procedure, e.g., to identify regions of the brain to be targeted during the procedure. As another example, the user can reference the visualization 412 to assist in identifying drugs to be administered to the subject.

Figure 5A:
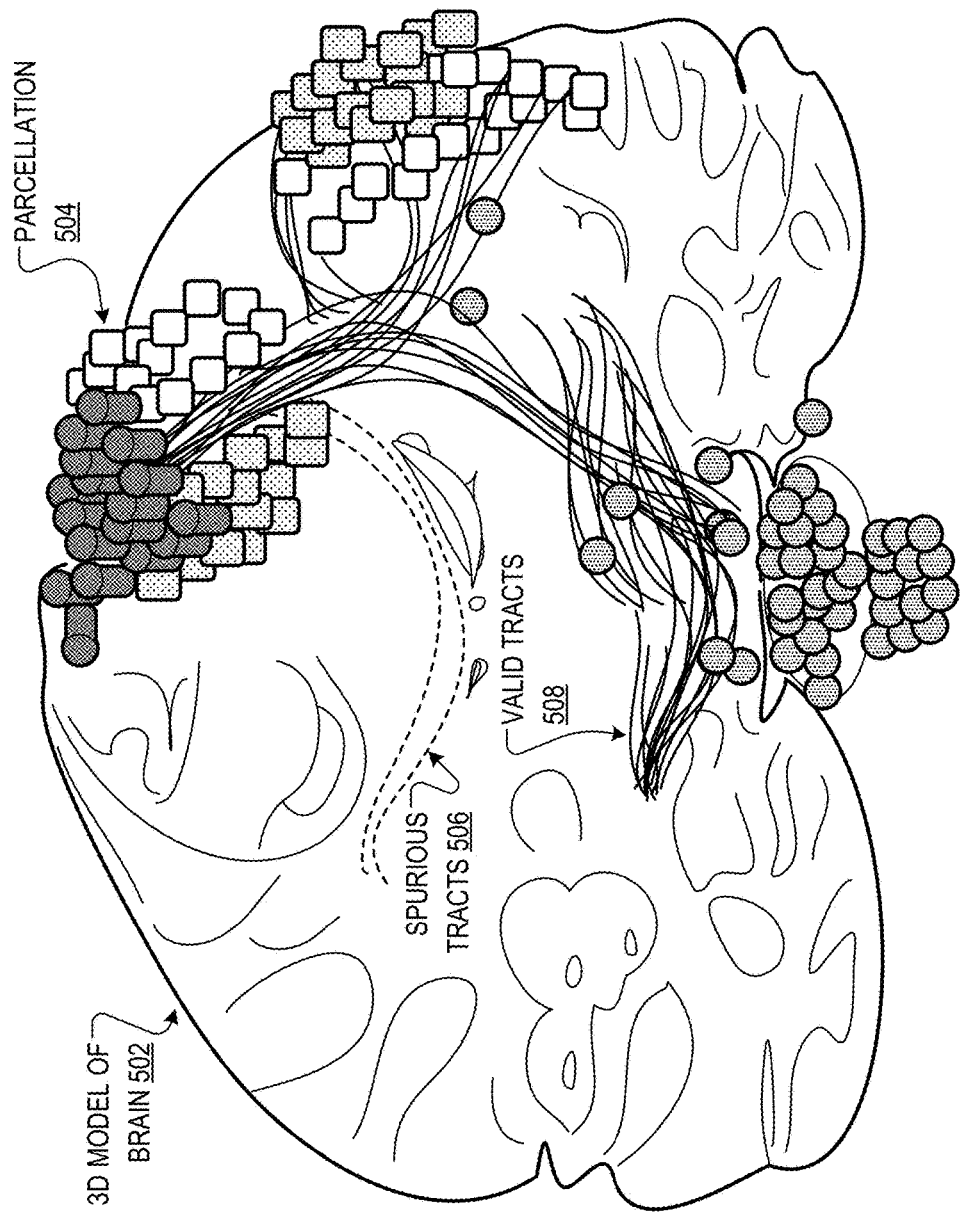

FIG. 5A illustrates a (simplified) example of a network visualization 412 that can be generated by the interface system 400. The valid tracts 508 and the spurious tracts 506 are represented as part of a 3D model of the brain 502 that additionally represents other features of the brain, e.g., the locations of certain parcellations, e.g., the parcellation 504. The spurious tracts 506 are visually distinguished from the valid tracts 508, in this example, as a result of being represented by dashed lines, i.e., in contrast to the valid tracts 508, which are represented as solid lines.

Generally, a tract processing system (e.g., the tract processing system 100 described with reference to FIG. 1) can identify spurious tracts in a network by applying a filtering criterion to a set of tracts that are predicted to be included in the network. However, the filtering criterion can, in some cases, incorrectly identify certain valid tracts as being spurious tracts. If the network visualization 412 entirely excluded the tracts identified as being spurious tracts, then the tract filtering operation would operate without user supervision and a user could not detect when valid tracts have been improperly filtered. On the other hand, refraining from performing the network filtering to identify spurious tracts may diminish the accuracy and interpretive value of the network visualization. Thus by including the spurious tracts 408, but visually distinguishing them from the valid tracts, the network visualization 412 can achieve the benefits of automated tract filtering (e.g., increased accuracy and interpretive value) while reducing any associated risks (e.g., valid tracts being improperly filtered).

Returning to the description of FIG. 4, the update engine 414 can update the network visualization 412 that the interface system 400 provides to the user computing device, e.g., in response to user selection data received from the user by way of the user interface. A few examples of updates that the update engine 414 can apply to the network visualization in response to the user selection data are described next.

In one example, a user can request that the filtering of the network be partially or completely reversed, e.g., such that at least some of the tracts identified as being spurious tracts are re-designated as being valid tracts. In some implementations, the user interface may include an interactive element (e.g., button) that, when selected by the user, indicates that the filtering of the network should be completely reversed, i.e., such that all of the tracts identified as spurious tracts are re-designated as being valid tracts. In some implementations, the user interface may include interactive tools that enable the user to select groups of one or more spurious tracts, thus indicating that the selected spurious tracts should be re-designated as being valid tracts.

In response to receiving user selection data indicating that selected spurious tracts should be re-designated as being valid tracts, the update engine 414 can update the network visualization 412, e.g., by harmonizing the visual appearance of the selected tracts with the visual appearance of the valid tracts. For example, the update engine 414 can update the color and/or transparency of the selected tracts to match the color and/or transparency of the valid tracts in the network visualization 412. Thus the interface system 400 can enable the user to increase the accuracy of the network visualization, e.g., by correcting errors introduced by the filtering of the tracts in the network.

Figure 5B:
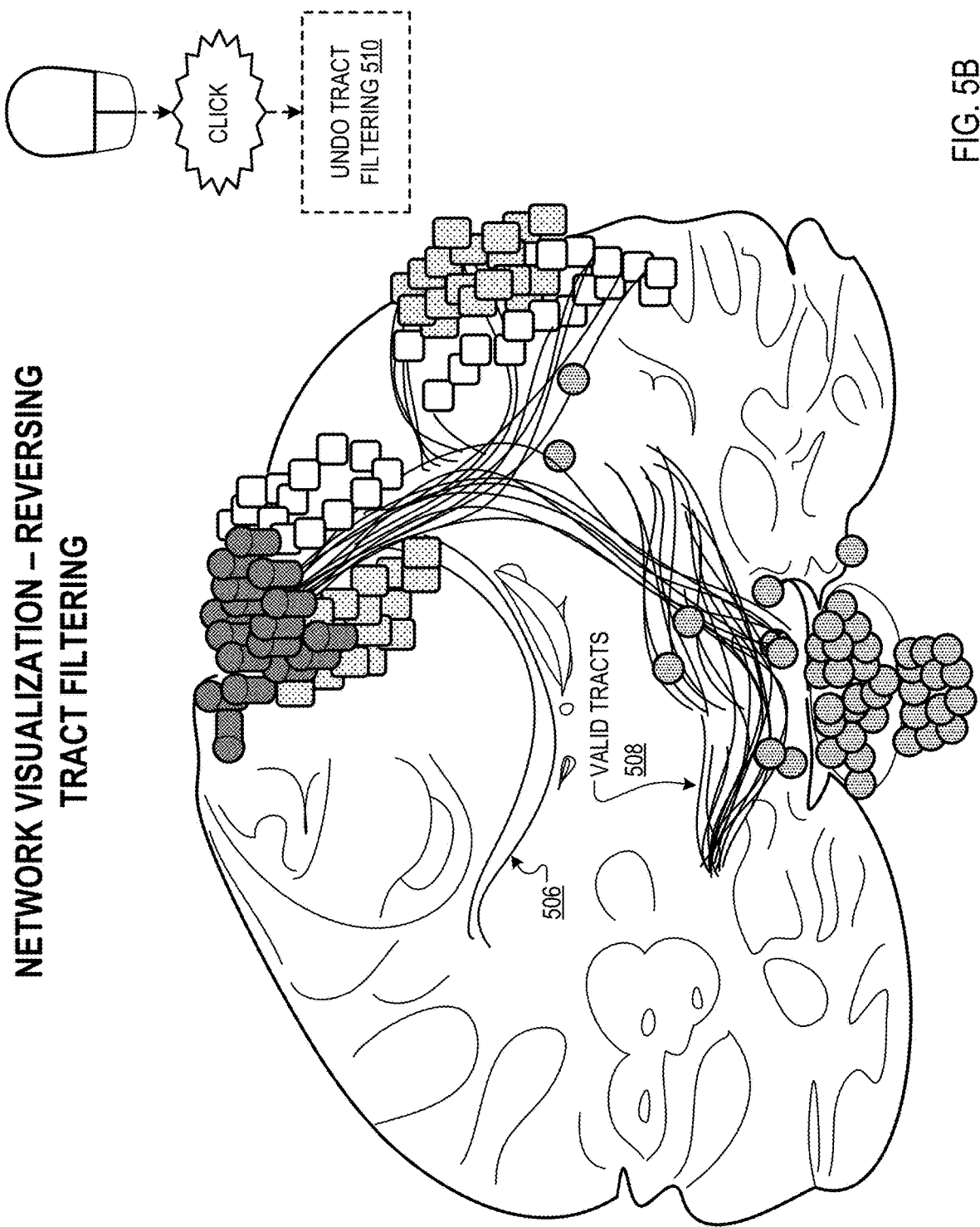

FIG. 5B illustrates an example of an updated version of the network visualization of FIG. 5A, where the tracts 506, which were previously designated as being spurious tracts, have been re-designated as being valid tracts. As part of re-designating the tracts 506 as being valid tracts, the update engine 414 harmonizes the appearance of the tracts 506 with the appearance of the valid tracts 508, e.g., such that they are both shown as solid lines. In this example, the user reversed the filtering of the tracts 506 by selecting an interactive element of the user interface, e.g., an "undo tract filtering" button 510.

In another example, a user can request that the spurious tracts be removed from the network visualization 412. In response to receiving user selection data indicating that the spurious tracts should be removed from the network visualization 412, the update engine 414 can update the network visualization 412 to remove the spurious tracts. "Removing" the spurious tracts from the network visualization 412 can refer to hiding the spurious tracts, i.e., such that they are no longer visually depicted in the network visualization 412.

FIG. 5C illustrates an example of an updated version of the network visualization of FIG. 5A, where spurious tracts shown in the network visualization of FIG. 5A have been removed from the network visualization of FIG. 5C. In this example, the user removed the spurious tracts by selecting an interactive element of the user interface, e.g., a "hide filtered tracts" button 512.

In another example, a user can request an update to the filtering criterion used to identify spurious tracts in the network. In response to receiving user selection data requesting an update to the filtering criterion, the update engine 414 can update the filtering criterion and then re-compute the filtered tract data 406 and the spurious tract data 408 for the network 402 in accordance with the updated filtering criterion. More specifically, the update engine 414 can apply the updated filtering criterion to a set of tracts that are predicted to be included in the network. The update engine 414 can identify any tract that satisfies the updated filtering criterion as being a spurious tract included in the updated spurious tract data 408, and identify the remaining tracts (i.e., that do not satisfy the updated filtering criterion) as being valid tracts included in the updated filtered tract data 406. The update engine 414 then updates the network visualization 412 based on the updated filtered tract data 406 and updated spurious tract data 408.

A user can request an update to the filtering criterion used to identify spurious tracts in the network in any of a variety of possible ways. In one example, the filtering criterion may be defined by a blocking surface, e.g., such that any tract that intersects the blocking surface can be identified as being a spurious tract, as described above with reference to FIG. 2. In this example, the user can initially request to have a representation of the blocking surface for the network included in the network visualization. The user interface may enable the user to manually specify adjustments to the spatial position and orientation of the blocking surface, e.g., by translating, rotating, and/or elastically deforming the blocking surface. The updated blocking surface may then define the updated filtering criterion used by the update engine 414 to update the network visualization 412.

Figure 5D:
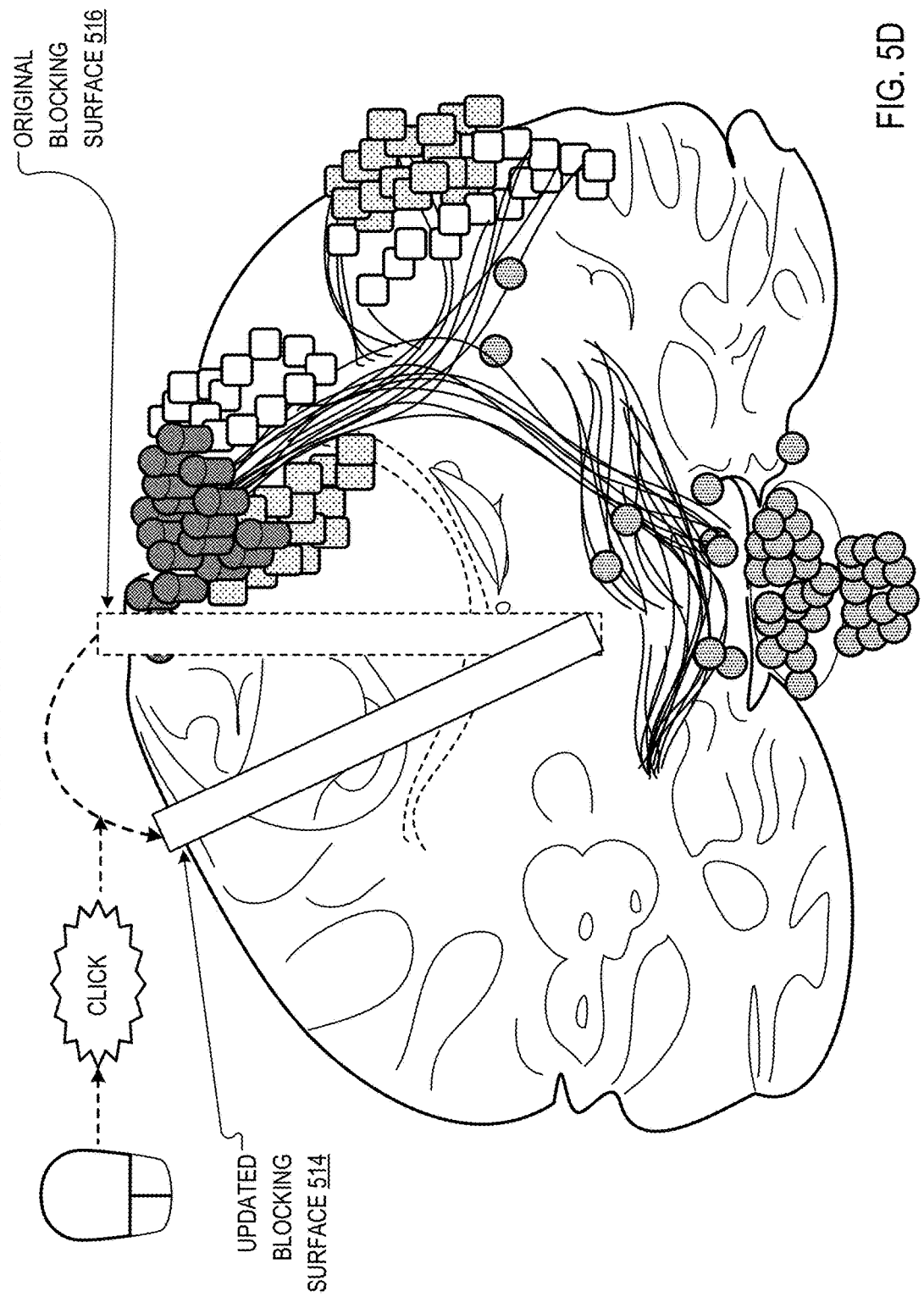

FIG. 5D illustrates an example of an updated version of the network visualization of FIG. 5A, where the user requests that the blocking surface 516 used to identify spurious tracts in the network be displayed in the network visualization. The user then specifies an adjustment to the blocking surface 516, in particular, by rotating the original blocking surface 516 to generate an updated blocking surface 514. The updated blocking surface 514 defines an updated filtering criterion for identifying spurious tracts in the network, and the update engine 414 can update the network visualization in accordance with the updated filtering criterion, as described above.

A user can request any of a variety of other appropriate updates to the network visualization, i.e., in addition to those described above, by way of the user interface. For example, a user can request an updated view of the network, e.g., by specifying appropriate panning or zooming operations. As another example, a user can request that one or more additional networks be added to the visualization.

Figure 6:
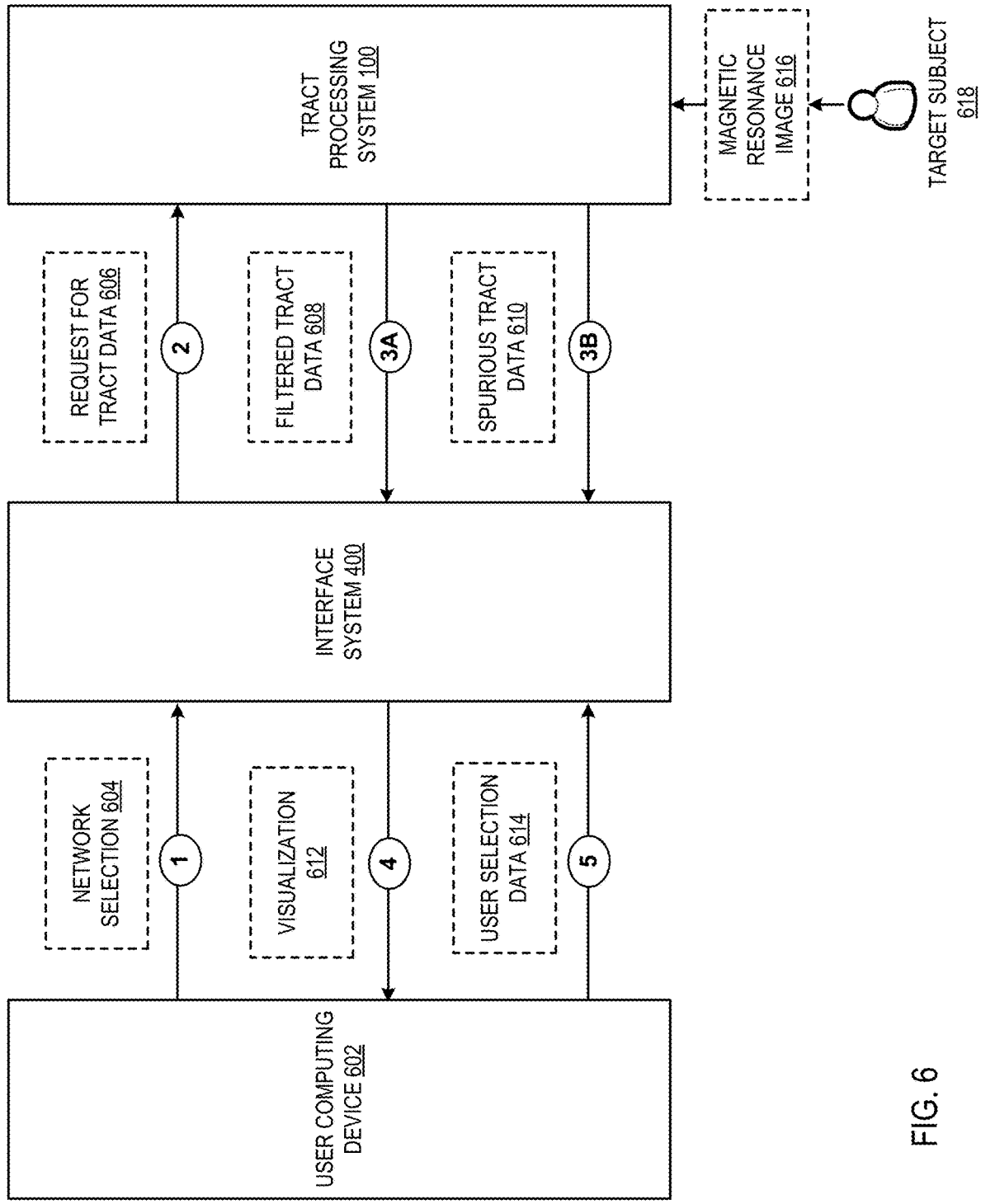
FIG. 6 illustrates a flow of data between: (i) a user computing device, (ii) an interface system, and (iii) a tract processing system.

FIG. 6 illustrates a flow of data between: (i) a user computing device 602, (ii) an interface system 400 (e.g., as described with reference to FIG. 4), and (iii) a tract processing system 100 (e.g., as described with reference to FIG. 1).

A user of the user computing device 602 can request to be provided with a visualization of a network 604 in the brain of a target subject 618. For example, the user can select the network, e.g., from a predefined set of networks, by way of a user interface made available on the user computing device 602.

In response to receiving the network selection 604, the interface system 400 requests 606 tract data for the network from the tract processing system 100.

In response to receiving the request 606 for tract data for the network, the tract processing system 100 provides: (i) filtered tract data 608 for the network, and (ii) spurious tract data 610 for the network, to the interface system 400. The filtered tract data 608 identifies tracts, in the brain of the target subject, that are predicted to be included in the network. The spurious tract data 610 identifies tracts, in the brain of the target subject, that were initially predicted to be included in the network but which were subsequently identified as being spurious tracts that are not included in the network.

The tract processing system 100 generates the filtered tract data 608 and the spurious tract data 610 for the network by processing an MRI image 616 of the brain of the target subject 618. The tract processing system 100 may have pre-computed the filtered tract data 608 and the spurious tract data 610, or the tract processing system 100 may dynamically compute the filtered tract data 608 and the spurious tract data 610 in response to receiving the request 606 from the interface system 400.

After receiving the filtered tract data 608 and the spurious tract data 610 for the network from the tract processing system 100, the interface system 400 renders a visualization 612 of the network and provides the visualization 612 for display on the user computing device 602. The visualization 612 of the network can visually distinguish the filtered tract data 608 from the spurious tract data 610, e.g., by showing the spurious tracts from the spurious tract data 610 with a different color and/or transparency than the valid tracts from the filtered tract data 608.

The user of the user computing device 602 can interact with the user interface to generate user selection data 614 requesting modifications to the visualization 612 of the network. For example, the user can request that some or all of the spurious tracts be re-designated as being valid tracts, that the spurious tracts be removed/hidden, or that the filtering criterion used to identify the spurious tracts be modified. In response to receiving the user selection data 614, the interface system 400 can update the network visualization 612 in accordance with the user selection data, and provide the updated network visualization for display on the user computing device 602.

Figure 7:
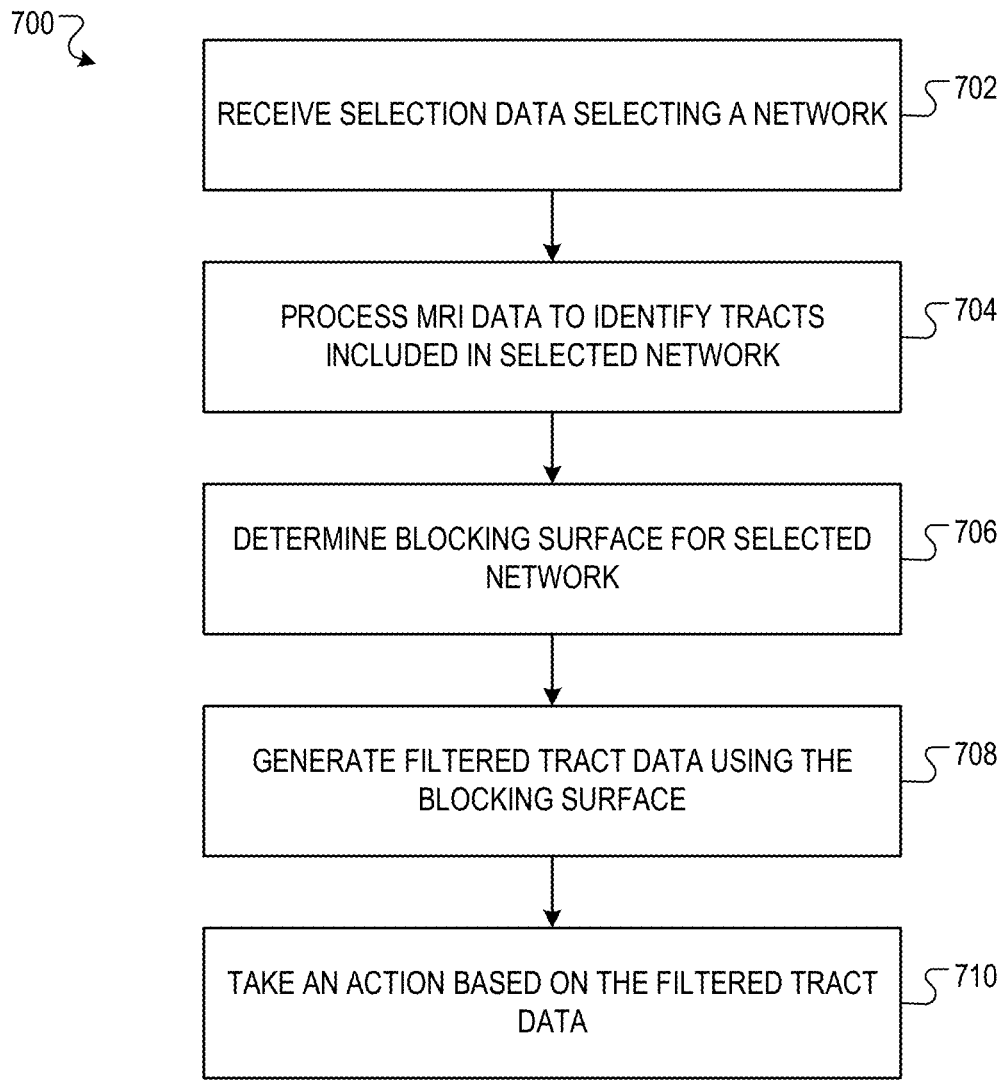
FIG. 7 is a flow diagram of an example process for generating filtered tract data for a network.

FIG. 7 is a flow diagram of an example process 700 for generating filtered tract data for a network. For convenience, the process 700 will be described as being performed by a system of one or more computers located in one or more locations. For example, a tract processing system, e.g., the tract processing system 100 of FIG. 1, appropriately programmed in accordance with this specification, can perform the process 700.

The system receives selection data selecting a network of a brain (702). The system can receive the selection data from a user, e.g., by way of a user interface made to the user on a user computing device.

The system processes magnetic resonance image data of the brain to identify a set of tracts that are predicted to be included in the selected network (704). For example, the system can perform tractography on the magnetic resonance image data to identify tracts in the brain, and then classify certain tracts as being included in the selected network.

The system determines a blocking surface for the selected network (706). For example, the system can receive data identifying a set of blocking parcellations corresponding to the selected network. The system can then determine, based on a respective position in the brain of each blocking parcellation, a set of parameters defining the blocking surface.

The system generates filtered tract data by filtering the set of tracts that are predicted to be included in the selected network to remove tracts that intersect the blocking surface (708).

The system takes an action based at least in part on the filtered tract data (710). For example, the system can generate a visualization of the filtered tract data for display on the user computing device.

Figure 8:
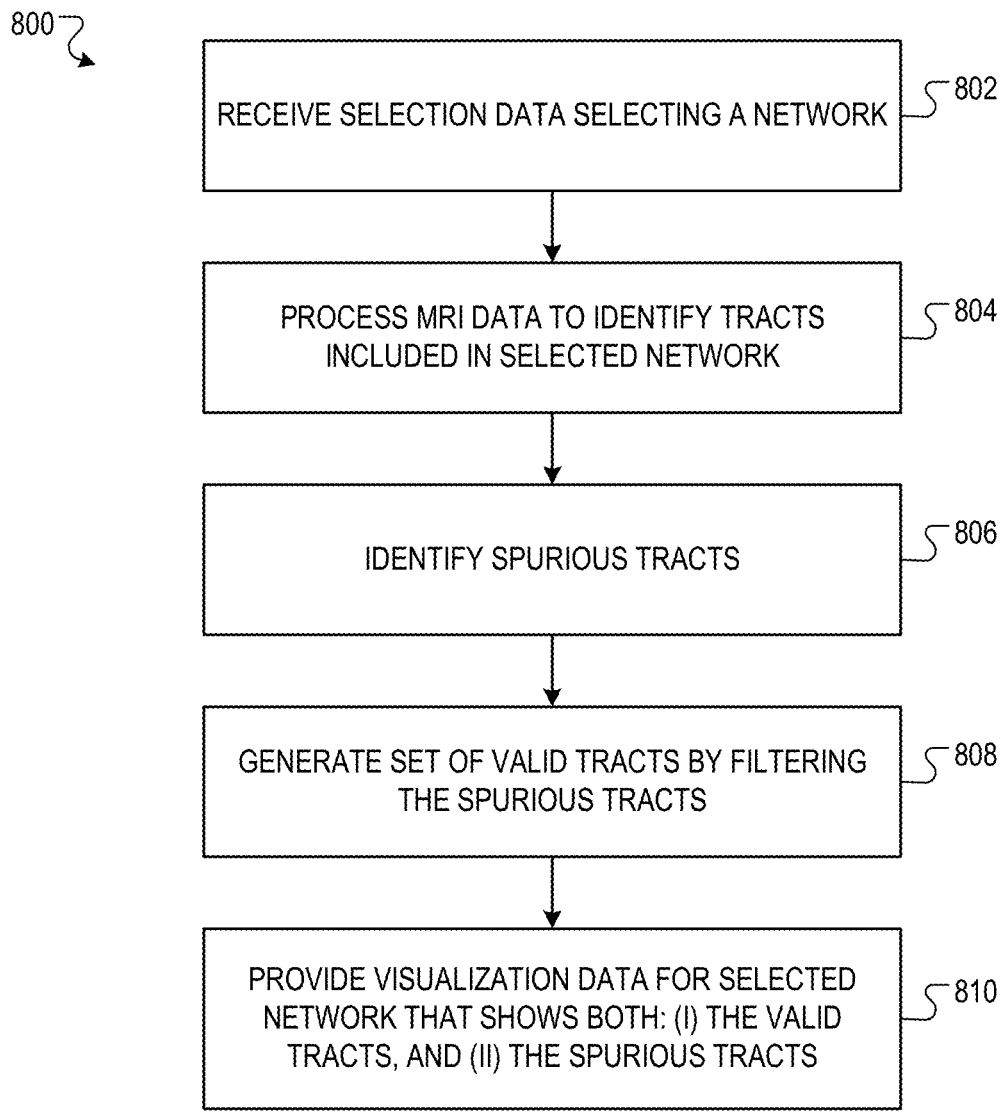
FIG. 8 is a flow diagram of an example process for generating a visualization of a network.

FIG. 8 is a flow diagram of an example process 800 for generating a visualization of a network. For convenience, the process 800 will be described as being performed by a system of one or more computers located in one or more locations. For example, an interface system, e.g., the interface system 400 of FIG. 4, appropriately programmed in accordance with this specification, can perform the process 800.

The system receives selection data selecting a network in a brain of a subject (802). The system can receive the selection data from a user, e.g., by way of a user interface made to the user on a user computing device.

The system processes magnetic resonance image data of the brain to identify a set of tracts that are predicted to be included in the selected network (804). For example, the system can perform tractography on the magnetic resonance image data to identify tracts in the brain, and then classify certain tracts as being included in the selected network.

The system processes the set of tracts that are predicted to be included in the selected network to identify a proper subset of the set of tracts as being spurious tracts (806). For example, the system can apply a filtering criterion based on a blocking surface to the set of tracts that are predicted to be included in the selected network to identify the spurious tracts.

The system generates a set of valid tracts by filtering the spurious tracts from the set of tracts that are predicted to be included in the selected network (808).

The system provides, for display on the user computing device, visualization data for the selected network showing a three-dimensional spatial representation of both: (i) the valid tracts, and (ii) the spurious tracts (810). The spurious tracts are visually distinguished from the valid tracts in the visualization.

Figure 9:
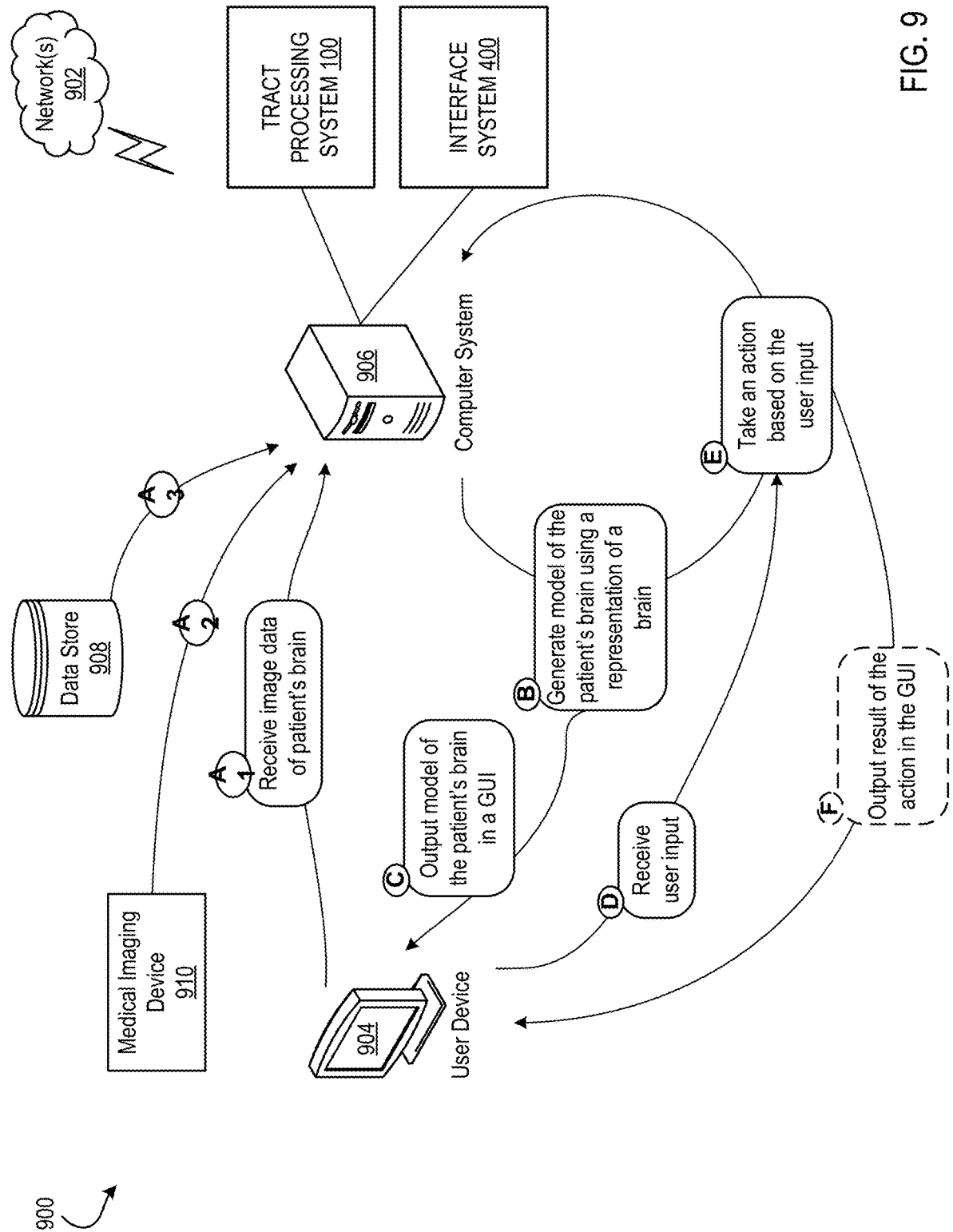
FIG. 9 is a conceptual diagram illustrating a computing environment for generating a GUI representation of a particular brain.

FIG. 9 is a conceptual diagram illustrating a computing environment 900 for generating a GUI representation of a particular brain. The computing environment 900 can include a user device 904, a computer system 906, a data store 908, and a medical imaging device 910, which can communicate (e.g., wired and/or wirelessly) via network(s) 902.

The user device 904 can be used by a medical professional, such as a clinician, surgeon, doctor, nurse, researcher, or other professional. The user device 904 and technologies described herein can be used by any other user. The user device 904 can be any one of a computer, laptop, tablet, mobile device, mobile phone, and/or smartphone. Sometimes, the user device 904 can be integrated into or otherwise part of one or more other devices in a medical setting, such as the medical imaging device 910 and/or the computer system 906. The medical professional can use the user device 904 to view information about a patient's brain. For example, using the disclosed technology, the medical professional can view, at the user device 904, 3D representations of a particular patient's brain and make determinations about what diagnosis, treatment, and/or surgical procedures to perform. The medical professional can also view other/additional information about the particular patient at the user device 904 to make more informed decisions with regards to the particular patient's diagnosis, treatment, surgery, or other medical or research purposes. Thus, the user device 904 can provide hardware that can support the GUIs, software, and applications described herein, such as a singular and interactive brain navigation system that makes it easier and more intuitive for the medical professionals to make medical and research determinations.

The computer system 906 can be a remote computing system, a cloud-based system or service, and/or integrated with or otherwise part of one or more devices in a medical setting (e.g., such as the user device 904 and/or the medical imaging device 910). The computer system 906 can be a computer, processor, a network of computers, a server, and/or a network of servers. Sometimes, each medical setting (e.g. a hospital) can have one or more computer systems 906. Sometimes, the computer system 906 can be used across multiple medical settings (e.g., multiple hospitals). The computer system 906 can be configured to generate interactive representations of patients' brains based off image data of the brains. The computer system 906 can also generate GUIs to display the interactive representations of the brains at the user device 904.

Sometimes, the computer system 906 can clean the image data by removing personally identifying information (e.g., protected health information (PHI)) from that data. Cleaning the image data can be beneficial to preserve patient privacy, especially if the interactive representations of patients' brains are used for medical research, clinical studies, or otherwise are stored in the data store 908 for future retrieval and use. Removing personally identifying information can also be advantageous if the computer system 906 is remote from the user device 904 and the interactive representations of the brain are generated at the computer system 906 that is outside a secure hospital infrastructure or other network where the image data may be generated and/or the interactive representations of the brain may be outputted. In other words, removing personally identifying information can be advantageous to preserve patient privacy when patient data is communicated between different networks and/or infrastructure.

The computer system 906 can implement the tract processing system 100 described with reference to FIG. 1 and the interface system 400 described with reference to FIG. 4. The computer system 906 can implement the operations of the tract processing system 100 and the interface system 400, as an alternative to or in combination with the other operations described with reference to FIG. 7.

The data store 908 can be a remote data store, cloud-based, or integrated into or otherwise part of one or more other components in the medical setting (e.g., such as the user device 904 and/or the computer system 906). The data store 908 can store different types of information, including but not limited to image data of patient brains (e.g., from the medical imaging device 910), cleaned image data (e.g., from the computer system 906), 3D representations of patient brains or other interactive representations of patient brains (e.g., from the computer system 906), connectivity data associated with patient brains, determinations, actions, or other user input taken by the medical professional (e.g., at the user device 904), patient information or records, or other relevant information that can be used in a medical setting.

The medical imaging device 910 can be any type of device and/or system that is used in the medical setting to capture image data of patient brains. The medical imaging device 910 can capture image data that includes but is not limited to x-rays, computed tomography (CT) scans, magnetic resonance imaging (Mills), electroencephalography (EEG) and/or ultrasound. One or more other types of image data can also be captured by the medical imaging device 910. The computer system 906 can be configured to receive any type of image data of a patient's brain and glean connectivity data about the brain from that image data to map the data onto a user-friendly interactive representation of a brain.

Still referring to FIG. 1, the computer system 906 can receive image data of a patient's brain from one or more of the user device 904 (step A1), the medical imaging device 910 (step A2), and the data store 908 (step A3). Sometimes, for example, when the user device 904 is part of the medical imaging device 910, the computer system can receive the image data captured by the medical imaging device 910 from only one device (e.g., the medical imaging device 910 or the user device 904). The image data can be captured by the medical imaging device 910 then sent directly, in real-time, to the computer system 906 (step A2) for real-time processing. Sometimes, the image data can be captured by the medical imaging device 910, then initially reviewed by the medical professional at the user device 904. Accordingly, the user device 904 can transmit the image data to the computer system 906 (step A1).

In some implementations, image data can be captured of multiple different brains by multiple different medical imaging devices 910. The image data can be stored in the data store 908 for future processing and analysis. The computer system 906 can then retrieve a batch or batches of the image data from the data store 908 (step A3) and process the image data in batch. Processing in batch can be advantageous to use fewer computational resources and reduce network bandwidth.

Once the computer system 906 receives the image data (steps A1-A3), the computer system can generate a model of the brain using a representation of a brain (step B). For example, the computer system 906 can map or model the patient's brain from the image data onto a 3D representation of a brain. The 3D representation can be a generic brain in 3-dimensional or other multi-dimensional space. The 3D representation can be a glass brain. Mapping the patient's brain onto the glass brain can be advantageous to provide vantage points of different structures, parcellations, and connectivity in the particular patient's brain. A medical professional can more easily analyze the particular patient's brain via the 3D representation of the brain rather than through the raw image data captured by the medical imaging device 910. As a result, the medical professional can generate more informed decisions and determinations with regards to the particular patient's diagnosis, treatment, surgery, condition, or other medical or research purposes.

Once the patient's brain is modeled using the representation of the brain (step B), the computer system 906 can output the model of the patient's brain in a GUI at the user device 904 (step C). For example, the computer system 906 can generate the GUI that displays the model of the patient's brain, then transmit the GUI to the user device 904 to be outputted. The model can represent the patient's brain overlaid on the glass brain. Sometimes, instead of outputting the model at the user device 904 (step C), the computer system 906 can store the model of the patient's brain in the data store 908. The model of the patient's brain can then be accessed/retrieved at a later time and presented to the medical professional or other user at the user device 904.

As mentioned throughout, when the model of the patient's brain is outputted at the user device 904, the GUI can allow the user, e.g., a medical professional, to take numerous actions in response to reviewing the model of the patient's brain. For example, the medical professional can determine what type of diagnosis, treatment, or surgical procedures to take with regards to this particular patient. The medical professional can also interact with the model of the patient's brain through use-selectable options and features in the GUI that is outputted at the user device 904. The medical professional can change views of the model of the patient's brain (e.g., rotate around the model, view only a left or right side of the patient's brain, etc.), select portions of the patient's brain from the model (e.g., select a particular lobe, node, parcellation, etc.), view other information about the patient (e.g., health records, prior medical visits, etc.), and simulate surgical procedures that can impact different parcellations or portions of the patient's brain (e.g., slicing a node or nodes that are connected to other nodes in the patient's brain). The medical professional can provide input to the user device 904, for example, via an input device, and the input can indicate the medical professional's interaction(s) with the model of the patient's brain. This input can then be received by the computer system 906 (step D).

The computer system 906 can take an action based on the received user input (step E). For example, if the medical professional changes or selects a different view of the model of the patient's brain, then the computer system 906 can generate an updated GUI display of the patient's brain that only includes the selected view. This updated GUI display can be outputted at the user device (step F). As another example, the medical professional can remove one or more nodes from the model of the patient's brain. The computer system 906 can receive this input (step D), simulate removal of the user-selected nodes (step E), then output results of removing such nodes from the brain at the user device 904 (step F). The medical professional can review the outputted results and take further actions in response. Further actions can include decisions about what nodes the medical professional should remove during the actual medical procedure and/or how to proceed with diagnosis, treatment, and/or the medical procedure.

Sometimes, the computer system 906 can take an action based on the user input (step E) that does not also include outputting a result of the action at the user device 904 (step F). For example, the medical professional can input notes about what actions the medical professional intends to take during a medical procedure, a diagnosis for the particular patient, and/or treatment for the patient. The computer system 906 can receive this input and store it in the data store 908 but may not output results from storing this input. This input can then be retrieved from the data store 908 and provided to one or more other devices (e.g., a report can be generated that indicates the patient's diagnosis and treatment). The report can then be provided to a device of the patient. The report can also be transmitted to devices of other medical professionals, such as those in a hospital infrastructure/network). The computer system 906 can take one or more other actions based on the user input (step E) and optionally output results of the action(s) at the user device 904 (step F).

Figure 10:
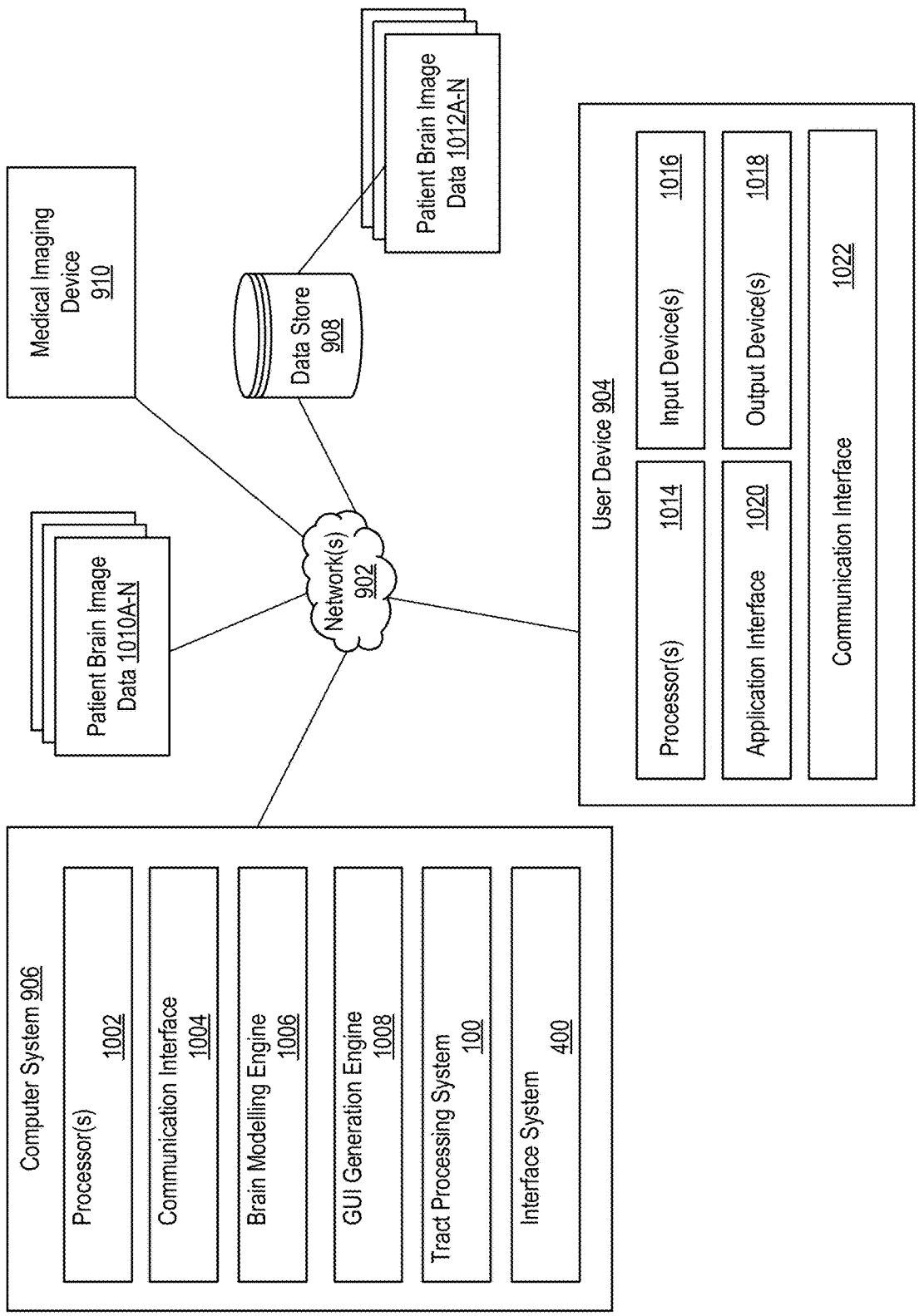
FIG. 10 illustrates components in a computing landscape that can be used to generate the GUI representation of the particular brain.

FIG. 10 illustrates components in a computing landscape that can be used to generate the GUI representation of the particular brain. As described above, the user device 104, computer system 906, data store 908, and medical imaging device 910 can communicate via the network(s) 102. One or more of the components 104, 906, 908, and 910 can also be integrated into a same computing system, network of devices, server, cloud-based service, etc. The network(s) 102 may be a wide-area network (WAN), such as the Internet, a cellular telecommunications network, or a private WAN. Connection via the network(s) 102 can include a traditional dial-up modem, a high-capacity (e.g., cable) connection such as a broadband modem, and/or a wireless modem.

The computer system 906 can include processor(s) 1002, communication interface 1004, brain modelling engine 1006, GUI generation engine 1008, the tract processing system 100 described with reference to FIG. 1, and the interface system 400 described with reference to FIG. 4. The processor(s) 1002 can be configured to perform one or more operations described herein. Although not depicted, the computer system 906 can also include at least one memory unit, which may have semiconductor random access memory (RAM) and semiconductor read only memory (ROM).

One or more of the techniques and processes described herein can be implemented as software application programs executable by the processor(s) 1002 in the computer system 906. Moreover, one or more of the techniques and processes described herein can be executed in browsers at remote terminals, systems, or devices (e.g., the user device 104 and/or another computer system), thereby enabling a user of the remote terminals, systems, or devices to access the software application programs that are executing on the computer system 906. For example, steps for any of the techniques and processes described herein can be effected by instructions in the software application programs that are carried out within the computer system 906. Software instructions may be formed as one or more code modules (e.g., using PYTHON or equivalent language modules installed on the computer system 906 and/or the remote terminals, systems, or devices), each for performing one or more particular tasks. The software instructions can also be divided into separate parts. For example, a first part and the corresponding code module(s) can perform the techniques and processes described herein and a second part and the corresponding code module(s) can manage a user interface (e.g., the GUIs described herein) between the first part and the medical professional at the user device 904.

Moreover, the software may be stored in a non-transitory, tangible, computer readable medium, including storage devices described throughout this disclosure. The software can be loaded into the computer system 906 from the computer readable medium, and then executed by the computer system 906. A computer readable medium having such software or computer program recorded on the computer readable medium can be a computer program product. Examples of transitory or non-tangible computer readable transmission media that may also participate in the provision of software, application programs, instructions and/or data include radio or infra-red transmission channels as well as a network connection to another computer or networked device, and the Internet or Intranets, including e-mail transmissions and information recorded on Websites and the like.

Still referring to the computer system 906, the brain modelling engine 1006 can be configured to map a patient's brain onto a representation of a brain (e.g., refer to step B in FIG. 1). For example, the brain modelling engine 1006 can receive patient brain image data 1010A-N, which can be used to generate a model of the patient's brain. The patient brain image data 1010A-N can be received from the medical imaging device 910. The patient brain image data 1010A-N can also be received from the user device 104. In some implementations, as described in reference to FIG. 1, the computer system 906 can retrieve patient brain image data 1012A-N from the data store 908. The patient brain image data 1012A-N can then be used by the brain modelling engine 1006 to model the patient's brain.

Sometimes, modelling the brain can include identifying connectivity data for the particular brain. Modelling the brain can then include mapping the connectivity data over the representation of a generic brain. In yet some implementations, modelling the patient's brain can include identifying hubs, parcellations, deep nodes, lateral nodes, and other portions of the patient's brain that can be mapped onto the representation of the generic brain. Moreover, the brain modelling engine 1006 can be configured to identify personally identifying information in the image data of the brain and extract that information before mapping the patient's brain onto the representation of the generic brain. The brain modelling engine 1006 can use one or more machine learning models to accurately map the particular patient's brain data onto a representation of the generic brain.

In some implementations, for example, Digital Imaging and Communications in Medicine (DICOM) images of a particular brain to be parcellated can be processed by the brain modelling engine 1006. DICOM is an international standard for transmitting, storing, retrieving, processing and/or displaying medical imaging information. A registration function for the particular brain can be determined in a Montreal Neurological Institute (MNI) space (a common coordinate space) described by a set of standard brain data image sets, a registered atlas from a human connectome project can be determined, and diffusion tractography of the DICOM images can be performed to determine a set of whole brain tractography images of the particular brain (in neuroscience, tractography can be thought of as a 3D modelling technique used to represent white matter tracts visually). For each voxel in a particular parcellation in the registered atlas, voxel level tractography vectors showing connectivity of the voxel with voxels in other parcellations can be determined, the voxel can be classified based on the probability of the voxel being part of the particular parcellation, and determining of the voxel level tractography vectors and the classifying of the voxels for all parcellations of the HCP-MMP1 Atlas can be repeated to form a personalised brain atlas (PBs Atlas) containing an adjusted parcellation scheme reflecting the particular brain.

The GUI generation engine 1008 can be configured to generate GUI displays of the modelled brain. The GUI generation engine 1008 can receive the modelled brain from the brain modelling engine 1006 and generate an appropriate GUI for displaying the modelled brain to the medical professional (e.g., refer to FIG. 3). The GUI generation engine 1008 can also transmit the generated GUI(s) to the user device 104 to be outputted/presented to the medical professional.

Moreover, whenever user input is received from the user device 104 that includes performing some action in response to the outputted model of the brain, the input can be received by the computer system 906. The brain modelling engine 1006 can take some action (e.g., refer to step E in FIG. 1) in response to receiving the user input (e.g., refer to step D in FIG. 1). That action can include, for example, simulating removal of one or more nodes in the patient's brain. The GUI generation engine 1008 can generate updated GUI displays based on the actions taken by the brain modelling engine 1006 (e.g., refer to step F in FIG. 1). The GUI generation engine 1008 can then transmit the updated GUI displays to the user device 104 to be outputted to the medical professional.

Sometimes, one or more of the components of the computer system 906, such as the brain modelling engine 1006 and the GUI generation engine 1008 can be part of one or more different systems. For example, the brain modelling engine 1006 can be part of a software application program that can be loaded and/or executed at another device, such as the user device 104 and/or the medical imaging device 906. As another example, the GUI generation engine 1008 can be part of a software application program that is executed at the user device 104 and the brain modelling engine 1006 can be executed at the computer system 906 or another remote computing system, server, or cloud-based server or system.

The user device 104 can include processor(s) 1014, input device(s) 1016, output device(s) 1018, application interface 1020, and communication interface 1022. The processor(s) 1014 can be configured to perform one or more operations described herein. Although not depicted, the user device 104 can also include at least one memory unit, which may have semiconductor random access memory (RAM) and semiconductor read only memory (ROM).

The input device(s) 1016 and output device(s) 1018 can include one or more of an audio-video interface that couples to a video display, speakers, and/or a microphone, keyboard, mouse, scanner, camera, touch screen display, other display screen(s) (e.g., LCDs), joystick, and/or other human interface device. The input device(s) 1016 can be configured to receive user input from the medical professional or other user. The output device(s) 1018 can be configured to output the model of the patient's brain and/or actions taken by the computer system 906 in response to the user input. The output device(s) 1018 can present a variety of GUI displays and information to the medical professional, where such displays and information are generated by the computer system 906. The output device(s) 1018 can also output information that is received or otherwise generated by the medical imaging device 910.

The application interface 1020 can be executable software or another program that is deployed at the user device 104. The GUIs generated by the computer system 906 can be displayed or otherwise outputted via the application interface 1020. In some implementations, the application interface 1020 can be executed at a browser of the user device 104. The medical professional can then access and view the GUIs via the Internet or other connection. Sometimes, the application interface 1020 can be executed as a software module/program/product at the user device 104. The application interface 1020 can provide the interactive GUIs to the medical professional and receive input from the medical professional (e.g., refer to FIG. 3).

The communication interfaces 1004 and 1022 can be configured to provide communication between and amongst the components described herein. For example, a modem can be integrated therein.

Figure 11:
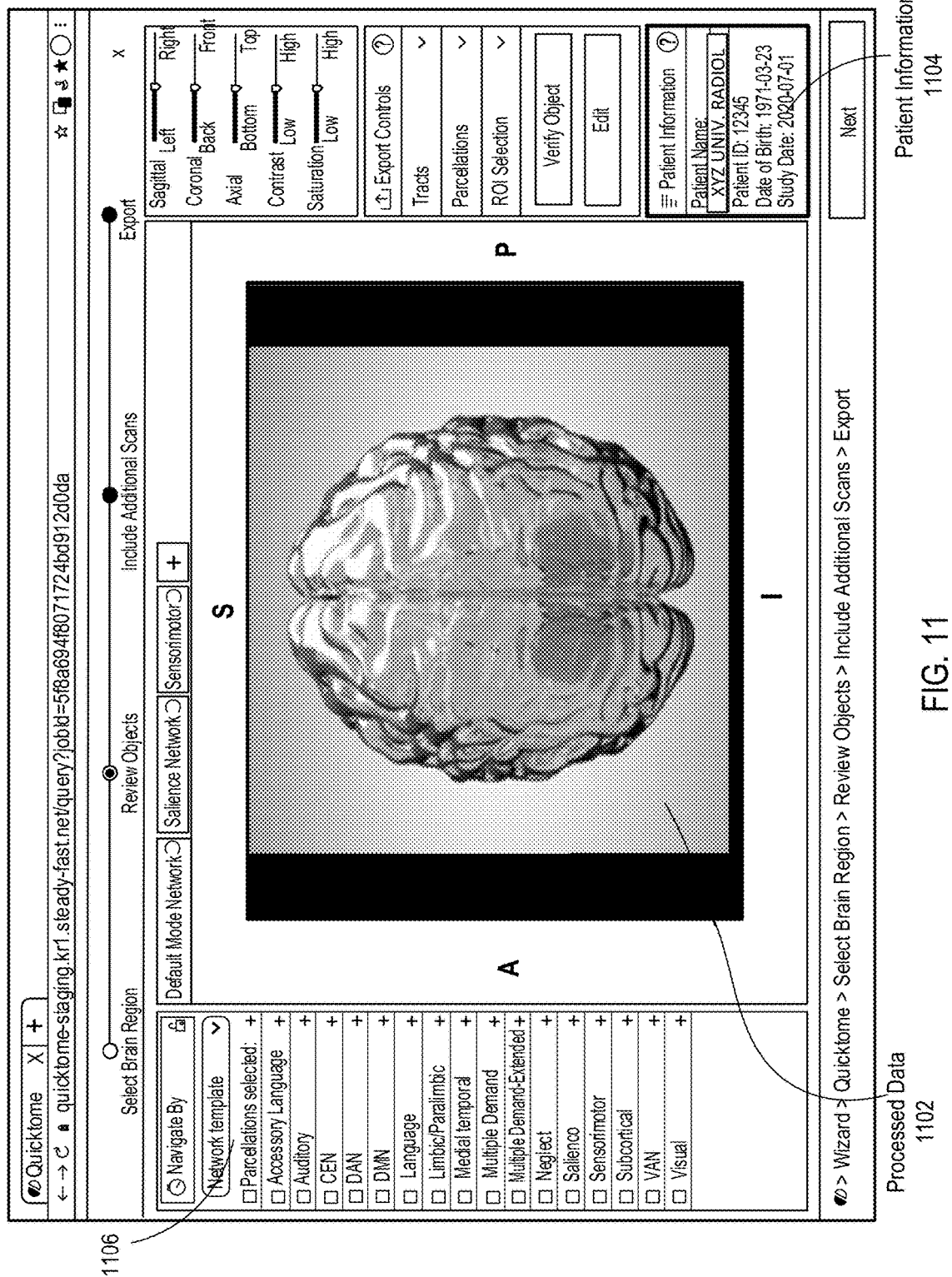
FIG. 11 illustrates a user-interactive GUI of the particular brain.

FIG. 11 illustrates a user-interactive GUI 1100 of the particular brain. The GUI 1100 can be outputted at the user device 904 described herein. The GUI 1100 outputs processed medical imaging data that is received of the particular brain. For example, the GUI 1100 can include processed data 1102, patient information 1104, and selectable options 1106. The processed data 1102 can include the particular brain as it is modeled on a representation of a brain. For example, the processed data 1102 can include a 3D representation of the particular brain, such as the particular brain overlaying a glass brain. The processed data 1102 also may not include other information that can appear in imaging data, such as patient information or other PHI. The PHI that corresponds to the processed data 1102 can optionally be outputted in the patient information 1104.

The GUI 1100 can provide a brain navigation system that is configured to display visual representations of an interior of the particular brain for clinical analysis and medical intervention, as well as visual representation of physiology of specific portions or objects of the brain (e.g. tracts, hubs, or parcellations of the brain). Such visual representations can reveal internal structures hidden by the skin and bones, and can be used to diagnose and treat various different diseases.

The medical professional can use the selectable options 1106 to specify particular actions (e.g. by making selections in the GUI 1100 presented at the user device 904) that the medical professional would like to take with regards to the processed data 1102. The medical professional can also choose options to export the processed data within an IT network of the hospital or other medical setting where the medical professional works. The medical professional can save the exported data, which can be used in future research and analysis.

The GUI 1100 presents only some options that may be presented to the medical professional with regards to the processed data 1102. One or more other options are also possible and can be presented in the GUI 1100 and/or in additional GUIs that are outputted at the user device 904.

Moreover, as described herein, the GUI 1100 can be part of a specialized computing system in the hospital IT infrastructure. Sometimes, the GUI 1100 can also be accessible via a web browser. The GUI 1100 may be configured—e.g. by authentication mechanisms such as login using username and/or password, biometric detection, and/or the like—to be used by only authorized individuals, such as clinicians (e.g. doctors, nurses, clinical staff, or the like), other medical professionals, or other authorized users (e.g. network administrator, technical staff, or the like) at the hospital or other medical setting. In some implementations, the GUI 1100 can also be in communication with or otherwise linked to one or more external devices, such as remote computers, that can be used to facilitate brain surgery or other medical procedures.

Although a brain image is useful for a medical professional, the medical professional can benefit more if they have additional information about components of the brain that is imaged. This additional information can be advantageous for the medical professional to make more informed decisions with regard to diagnosis, treatment, and medical procedures. Accordingly, as shown in FIG. 11, the GUI 1100 can provide the medical professional with tools (e.g., such as the selectable options 1106) that allow the medical professional to interact with the modelled version of the particular brain. The medical professional can provide input for selecting portions of the processed data 1102. The selected portions can be objects—e.g. brain tracts and/or brain parcellations—that the medical professional desires to see more information about, remove from the brain in a simulated procedure, or otherwise review and analyze. Accordingly, the medical professional can specify particular portions of the brain to analyze. The medical professional may also desire to identify and specify, on the GUI 1100, particular objects on several features, such as local properties of brain tissue, long-range connectivity patterns, structural markers, functional markers, and/or the like. The disclosed technology therefore can provide the medical professional with a more comprehensive, interactive, and user friendly interface for making determinations about a particular patient's brain condition(s).

Figure 12:
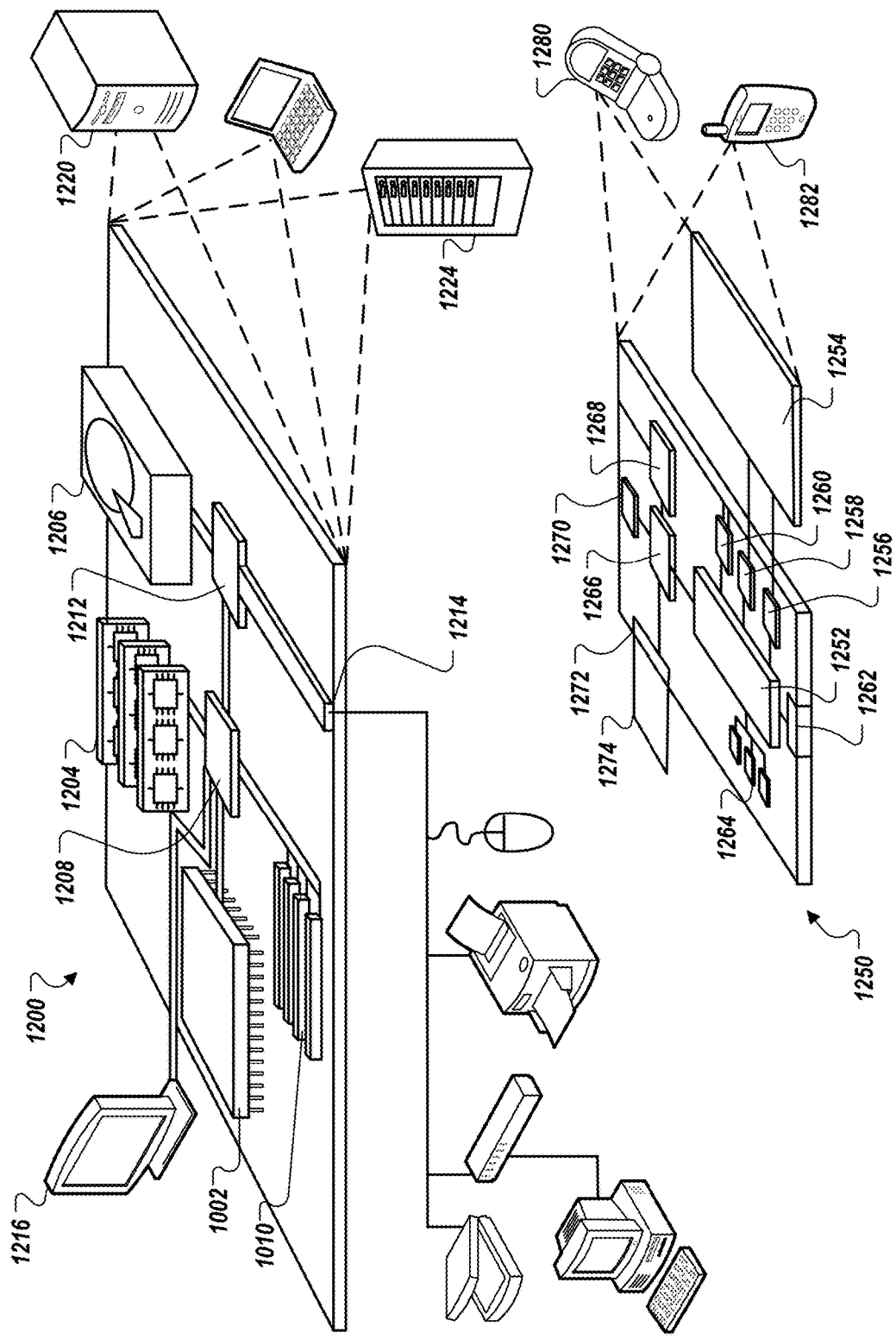
FIG. 12 shows an example of a computing device.

FIG. 12 shows an example of a computing device 1200 and an example of a mobile computing device that can be used to implement the techniques described here. The computing device 1200 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 1200 includes a processor 1202, a memory 1204, a storage device 1206, a high-speed interface 1208 connecting to the memory 1204 and multiple high-speed expansion ports 1210, and a low-speed interface 1212 connecting to a low-speed expansion port 1214 and the storage device 1206. Each of the processor 1202, the memory 1204, the storage device 1206, the high-speed interface 1208, the high-speed expansion ports 1210, and the low-speed interface 1212, are interconnected using various busses, and can be mounted on a common motherboard or in other manners as appropriate. The processor 1202 can process instructions for execution within the computing device 1200, including instructions stored in the memory 1204 or on the storage device 1206 to display graphical information for a GUI on an external input/output device, such as a display 1216 coupled to the high-speed interface 1208. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 1204 stores information within the computing device 1200. In some implementations, the memory 1204 is a volatile memory unit or units. In some implementations, the memory 1204 is a non-volatile memory unit or units. The memory 1204 can also be another form of computer-readable medium, such as a magnetic or optical disk.

The storage device 1206 is capable of providing mass storage for the computing device 1200. In some implementations, the storage device 1206 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 1204, the storage device 1206, or memory on the processor 1202.

The high-speed interface 1208 manages bandwidth-intensive operations for the computing device 1200, while the low-speed interface 1212 manages lower bandwidth-intensive operations. Such allocation of functions is exemplary only. In some implementations, the high-speed interface 1208 is coupled to the memory 1204, the display 1216 (e.g., through a graphics processor or accelerator), and to the high-speed expansion ports 1210, which can accept various expansion cards (not shown). In the implementation, the low-speed interface 1212 is coupled to the storage device 1206 and the low-speed expansion port 1214. The low-speed expansion port 1214, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 1200 can be implemented in a number of different forms, as shown in the figure. For example, it can be implemented as a standard server 1220, or multiple times in a group of such servers. In addition, it can be implemented in a personal computer such as a laptop computer 1222. It can also be implemented as part of a rack server system 1224. Alternatively, components from the computing device 1200 can be combined with other components in a mobile device (not shown), such as a mobile computing device 1250. Each of such devices can contain one or more of the computing device 1200 and the mobile computing device 1250, and an entire system can be made up of multiple computing devices communicating with each other.

The mobile computing device 1250 includes a processor 1252, a memory 1264, an input/output device such as a display 1254, a communication interface 1266, and a transceiver 1268, among other components. The mobile computing device 1250 can also be provided with a storage device, such as a micro-drive or other device, to provide additional storage. Each of the processor 1252, the memory 1264, the display 1254, the communication interface 1266, and the transceiver 1268, are interconnected using various buses, and several of the components can be mounted on a common motherboard or in other manners as appropriate.

The processor 1252 can execute instructions within the mobile computing device 1250, including instructions stored in the memory 1264. The processor 1252 can be implemented as a chipset of chips that include separate and multiple analog and digital processors. The processor 1252 can provide, for example, for coordination of the other components of the mobile computing device 1250, such as control of user interfaces, applications run by the mobile computing device 1250, and wireless communication by the mobile computing device 1250.

The processor 1252 can communicate with a user through a control interface 1258 and a display interface 1256 coupled to the display 1254. The display 1254 can be, for example, a TFT (Thin-Film-Transistor Liquid Crystal Display) display or an OLED (Organic Light Emitting Diode) display, or other appropriate display technology. The display interface 1256 can comprise appropriate circuitry for driving the display 1254 to present graphical and other information to a user. The control interface 1258 can receive commands from a user and convert them for submission to the processor 1252. In addition, an external interface 1262 can provide communication with the processor 1252, so as to enable near area communication of the mobile computing device 1250 with other devices. The external interface 1262 can provide, for example, for wired communication in some implementations, or for wireless communication in other implementations, and multiple interfaces can also be used.

The memory 1264 stores information within the mobile computing device 1250. The memory 1264 can be implemented as one or more of a computer-readable medium or media, a volatile memory unit or units, or a non-volatile memory unit or units. An expansion memory 1274 can also be provided and connected to the mobile computing device 1250 through an expansion interface 1272, which can include, for example, a SIMM (Single In Line Memory Module) card interface. The expansion memory 1274 can provide extra storage space for the mobile computing device 1250, or can also store applications or other information for the mobile computing device 1250. Specifically, the expansion memory 1274 can include instructions to carry out or supplement the processes described above, and can include secure information also. Thus, for example, the expansion memory 1274 can be provide as a security module for the mobile computing device 1250, and can be programmed with instructions that permit secure use of the mobile computing device 1250. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 1264, the expansion memory 1274, or memory on the processor 1252. In some implementations, the computer program product can be received in a propagated signal, for example, over the transceiver 1268 or the external interface 1262.

The mobile computing device 1250 can communicate wirelessly through the communication interface 1266, which can include digital signal processing circuitry where necessary. The communication interface 1266 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 1268 using a radio-frequency. In addition, short-range communication can occur, such as using a Bluetooth, WiFi, or other such transceiver (not shown). In addition, a GPS (Global Positioning System) receiver module 1270 can provide additional navigation- and location-related wireless data to the mobile computing device 1250, which can be used as appropriate by applications running on the mobile computing device 1250.

The mobile computing device 1250 can also communicate audibly using an audio codec 1260, which can receive spoken information from a user and convert it to usable digital information. The audio codec 1260 can likewise generate audible sound for a user, such as through a speaker, e.g., in a handset of the mobile computing device 1250. Such sound can include sound from voice telephone calls, can include recorded sound (e.g., voice messages, music files, etc.) and can also include sound generated by applications operating on the mobile computing device 1250.

The mobile computing device 1250 can be implemented in a number of different forms, as shown in the figure. For example, it can be implemented as a cellular telephone 1280. It can also be implemented as part of a smart-phone 1282, personal digital assistant, or other similar mobile device.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method comprising:
   receiving selection data selecting a network of a brain;
   processing magnetic resonance image data of the brain to identify a set of tracts that are predicted to be included in the selected network;
   determining a blocking surface for the selected network, comprising:

obtaining a set of parcellations for the selected network; and determining, based on a respective position in the brain of each parcellation in the set of parcellations, a set of parameters defining the blocking surface;

generating filtered tract data by filtering the set of tracts that are predicted to be included in the selected network to remove tracts that intersect the blocking surface; and taking an action based at least in part on the filtered tract data.

2. The method of claim 1, wherein determining the set of parcellations defining the blocking surface comprises:

determining a respective central position, in the brain, of each parcellation in the set of parcellations corresponding to the selected network; and determining the set of parameters defining the blocking surface based on the respective central position, in the brain, of each parcellation in the set of parcellations corresponding to the selected network.

3. The method of claim 2, wherein determining the set of parcellations defining the blocking surface based on the respective central position, in the brain, of each parcellation in the set of parcellations corresponding to the selected network comprises:

estimating a convex hull of the central positions of the parcellations in the set of parcellations corresponding to the selected network; and determining the set of parameters defining the blocking surface based on the convex hull of the central positions of the parcellations in the set of parcellations corresponding to the selected network.

4. The method of claim 3, wherein the blocking surface comprises a surface of the convex hull of the central positions of the parcellations in the set of parcellations corresponding to the selected network.

5. The method of claim 2, wherein determining the set of parameters defining the blocking surface based on the respective central position, in the brain, of each parcellation in the set of parcellations corresponding to the selected network comprises:

performing an optimization to determine a set of parameters defining a planar surface that minimizes an error between: (i) the planar surface, and (ii) the respective central position of each parcellation in the set of parcellations corresponding to the selected network.

6. The method of claim 5, wherein the optimization comprises a least-squares optimization.

7. The method of claim 2, wherein for each parcellation in the set of parcellations corresponding to the selected network, the central position of the parcellation is a centroid of the parcellation.

8. The method of claim 1, wherein the blocking surface is a two-dimensional surface.

9. The method of claim 1, wherein the blocking surface is a planar surface.

10. The method of claim 1, wherein the blocking surface is a surface of a convex polytope.

11. The method of claim 1, wherein the set of parcellations corresponding to the selected network comprises at least three parcellations.

12. The method of claim 1, wherein the magnetic resonance image data of the brain comprises diffusion-weighted magnetic resonance image data.

13. The method of claim 1, wherein the selected network of the brain is selected from a group comprising one or more of: a corticospinal network, a superior longitudinal fasciculus network, a cingulum network, a frontal aslant tract network, a uncinated fasciculus network, an inferior longitudinal fasciculus network, a middle longitudinal fascicle network, a vertical occipital fasciculus network, or an optic radiations network.

14. The method of claim 1, wherein generating filtered tract data by filtering the set of tracts that are predicted to be included in the selected network to remove tracts that intersect the blocking surface comprises:

identifying tracts that intersect the blocking surface as being spurious tracts.

15. The method of claim 1, wherein taking an action based at least in part on the filtered tract data comprises:

providing a visualization of the filtered tract data for display on a user computing device.

16. The method of claim 1, wherein taking an action based at least in part on the filtered tract data comprises:

using the filtered tract data to guide a surgical procedure.

17. The method of claim 1, wherein taking an action based at least in part on the filtered tract data comprises:

using the filtered tract data to select a drug to be administered to a subject.

18. The method of claim 1, wherein taking an action based at least in part on the filtered tract data comprises:

using the filtered tract data to plan a transcranial magnetic stimulation procedure.

19. A system comprising:

one or more computers; and one or more storage devices communicatively coupled to the one or more computers, wherein the one or more storage devices store instructions that, when executed by the one or more computers, cause the one or more computers to perform operations comprising:

receiving selection data selecting a network of a brain;

processing magnetic resonance image data of the brain to identify a set of tracts that are predicted to be included in the selected network;

determining a blocking surface for the selected network, comprising:

receiving data identifying a set of parcellations corresponding to the selected network; and determining, based on a respective position in the brain of each parcellation in the set of parcellations corresponding to the selected network, a set of parameters defining the blocking surface;

generating filtered tract data by filtering the set of tracts that are predicted to be included in the selected network to remove tracts that intersect the blocking surface; and taking an action based at least in part on the filtered tract data.

20. One or more non-transitory computer storage media storing instructions that when executed by one or more computers cause the one or more computers to perform operations comprising:

receiving selection data selecting a network of a brain;

processing magnetic resonance image data of the brain to identify a set of tracts that are predicted to be included in the selected network;

determining a blocking surface for the selected network, comprising:

receiving data identifying a set of parcellations corresponding to the selected network; and determining, based on a respective position in the brain of each parcellation in the set of parcellations corresponding to the selected network, a set of parameters defining the blocking surface;

generating filtered tract data by filtering the set of tracts that are predicted to be included in the selected network to remove tracts that intersect the blocking surface; and taking an action based at least in part on the filtered tract data.

\* \* \* \* \*